(12) United States Patent
Daly et al.

(10) Patent No.: US 12,303,580 B2
(45) Date of Patent: May 20, 2025

(54) SUNSCREEN COMPOSITIONS CONTAINING A COMBINATION OF A LINEAR ULTRAVIOLET RADIATION-ABSORBING POLYETHER AND OTHER ULTRAVIOLET-SCREENING COMPOUNDS

(71) Applicant: Kenvue Brands LLC, Summit, NJ (US)

(72) Inventors: Susan Daly, Basking Ridge, NJ (US); Julie Grumelard, Village-Neuf (FR)

(73) Assignee: Kenvue Brands LLC, Summit, NJ (US)

( * ) Notice: Subject to any disclaimer, the term of this patent is extended or adjusted under 35 U.S.C. 154(b) by 0 days.

(21) Appl. No.: 17/749,470

(22) Filed: May 20, 2022

(65) Prior Publication Data

US 2022/0280400 A1 Sep. 8, 2022

Related U.S. Application Data

(63) Continuation of application No. 16/308,050, filed as application No. PCT/US2017/036976 on Jun. 12, 2017, now abandoned.

(60) Provisional application No. 62/378,736, filed on Aug. 24, 2016, provisional application No. 62/362,251, filed on Jul. 14, 2016, provisional application No. 62/350,863, filed on Jun. 16, 2016.

(51) Int. Cl.
| | |
|---|---|
| *A61K 8/35* | (2006.01) |
| *A61K 8/39* | (2006.01) |
| *A61K 8/49* | (2006.01) |
| *A61K 8/86* | (2006.01) |
| *A61Q 17/04* | (2006.01) |

(52) U.S. Cl.
CPC ............... *A61K 8/35* (2013.01); *A61K 8/39* (2013.01); *A61K 8/496* (2013.01); *A61K 8/86* (2013.01); *A61Q 17/04* (2013.01)

(58) Field of Classification Search
CPC .......... A61Q 17/00; A61Q 17/04; A61K 8/35; A61K 8/39; A61K 8/86; A61K 8/496
See application file for complete search history.

(56) References Cited

U.S. PATENT DOCUMENTS

| | | |
|---|---|---|
| 4,107,290 A | 8/1978 | Jacquet et al. |
| 4,322,522 A | 3/1982 | Johnson et al. |
| 4,399,297 A | 8/1983 | Thoemel et al. |
| 4,528,311 A | 7/1985 | Beard et al. |
| 4,839,160 A | 6/1989 | Forestier et al. |
| 4,897,259 A | 1/1990 | Murray et al. |
| 5,039,782 A | 8/1991 | Langer et al. |
| 5,041,281 A | 8/1991 | Strobridge |
| 5,093,107 A * | 3/1992 | Matravers ............... A61K 8/37 424/59 |
| 5,138,089 A | 8/1992 | Sabatelli |
| 5,157,091 A | 10/1992 | Masataka et al. |
| 5,166,234 A | 11/1992 | Kawaguchi et al. |
| 5,250,652 A | 10/1993 | Langer et al. |
| 5,399,371 A | 3/1995 | Harris |
| 5,401,622 A | 3/1995 | Yamada |
| 5,459,222 A | 10/1995 | Rodgers et al. |
| 5,487,885 A | 1/1996 | Sovak et al. |
| 5,585,090 A | 12/1996 | Yoshioka et al. |
| 5,674,475 A | 10/1997 | Dahms et al. |
| 5,741,924 A | 4/1998 | Sovak et al. |
| 5,843,410 A | 12/1998 | Kim et al. |
| 5,869,030 A | 2/1999 | Dumler et al. |
| 5,869,099 A | 2/1999 | Keller et al. |
| 6,001,337 A | 12/1999 | Keller et al. |
| 6,048,516 A | 4/2000 | Bringhen et al. |
| 6,123,928 A | 9/2000 | Sovak et al. |
| 6,143,850 A | 11/2000 | Keller et al. |
| 6,183,728 B1 | 2/2001 | Forestier et al. |
| 6,193,959 B1 | 2/2001 | Bernasconi et al. |
| 6,294,156 B1 | 9/2001 | Lentini et al. |
| 6,391,287 B1 | 5/2002 | Baldo et al. |
| 6,413,393 B1 | 7/2002 | Van Antwerp et al. |
| 6,471,949 B2 | 10/2002 | Didier Candau et al. |
| 6,540,986 B2 | 4/2003 | Lukenbach et al. |
| 6,620,407 B1 | 9/2003 | Gers-Barlag et al. |
| 6,620,904 B2 | 9/2003 | Lemke |
| 6,767,547 B2 | 7/2004 | Gers-Barlag et al. |
| 6,800,274 B2 | 10/2004 | Bonda et al. |
| 6,814,959 B1 | 11/2004 | Muller et al. |
| 6,867,250 B1 | 3/2005 | Gupta et al. |
| 6,869,597 B2 | 3/2005 | Arnaud |
| 6,881,415 B1 | 4/2005 | Gers-Barlag et al. |
| 6,899,866 B2 | 5/2005 | Bonda |
| 6,905,674 B2 | 6/2005 | L'Alloret |
| 6,951,911 B2 | 10/2005 | Tagawa et al. |

(Continued)

FOREIGN PATENT DOCUMENTS

| | | |
|---|---|---|
| DE | 2024051 A | 5/1986 |
| EP | 407932 A | 1/1991 |

(Continued)

OTHER PUBLICATIONS

U.S. Appl. No. 15/007,552, filed Jan 27, 2016, 2016/0136073, May 19, 2016, Grant, U.S. Pat. No. 9,737,470, Aug. 22, 2017, Daly.
U.S. Appl. No. 15/007,564, filed Jan 27, 2016, 2016/0136074, May 19, 2016, Grant, U.S. Pat. No. 9,737,471, Aug. 22, 2017, Daly.
U.S. Appl. No. 15/648,503, filed Jul. 13, 2017, 2017/0312203, Nov. 2, 2017, Grant, U.S. Pat. No. 10,278,910, May 7, 2019, Daly.
U.S. Appl. No. 15/648,507, filed Jul. 13, 2017, 2017/0304174, Oct. 26, 2017, Abandoned, Daly.
U.S. Appl. No. 13/926,248, filed Jun. 25, 2013, 2014/0004063, Jan. 2, 2014, Grant, U.S. Pat. No. 9,248,092, Feb. 2, 2016, Daly.
U.S. Appl. No. 13/926,282, filed Jun. 25, 2013, 2014/0004064, Jan. 2, 2014, Grant, U.S. Pat. No. 9,254,254, Feb. 9, 2016, Daly.
U.S. Appl. No. 61/665,464, filed Jun. 28, 2012, Expired, Daly et al.
U.S. Appl. No. 13/710,531, filed Dec. 11, 2012, 2014/0004057, Jan. 2, 2014, Abandoned, Daly et al.
U.S. Appl. No. 14/565,909, filed Dec. 10, 2014, 2015/0093341, Apr. 2, 2015, Grant, U.S. Pat. No. 9,592,190, Mar. 14, 2017, Daly et al.

(Continued)

*Primary Examiner* — Hong Yu

(57) ABSTRACT

Sunscreen composition including a combination of a linear ultraviolet radiation absorbing polyether that includes a covalently bound UV-chromophore, and at least one non-polymeric UV-screening compounds.

1 Claim, No Drawings

(56) References Cited

U.S. PATENT DOCUMENTS

| | | |
|---|---|---|
| 6,962,692 B2 | 11/2005 | Bonda et al. |
| 6,989,151 B2 | 1/2006 | Gers-Barlag et al. |
| 7,008,618 B1 | 3/2006 | Hessefort et al. |
| 7,087,692 B2 | 8/2006 | Koshti et al. |
| 7,097,828 B2 | 8/2006 | Meyer et al. |
| 7,153,494 B2 | 12/2006 | Chodorowski et al. |
| 7,186,415 B1 | 3/2007 | Gers-Barlag et al. |
| 7,264,795 B2 | 9/2007 | Pflücker et al. |
| 7,427,640 B1 | 9/2008 | Katayama et al. |
| 7,465,438 B2 | 12/2008 | Schunicht et al. |
| 7,534,420 B2 | 5/2009 | Bonda et al. |
| 7,749,524 B2 | 7/2010 | Lu et al. |
| 7,850,954 B2 | 12/2010 | Leblanc et al. |
| 7,914,775 B2 | 3/2011 | Cottard et al. |
| 7,988,953 B2 | 8/2011 | Poschalko et al. |
| 7,993,680 B2 | 8/2011 | Clemente et al. |
| 8,003,132 B2 | 8/2011 | Clemente et al. |
| 8,025,868 B2 | 9/2011 | Clemente et al. |
| 8,211,850 B2 | 7/2012 | Andjelic et al. |
| 8,394,755 B2 | 3/2013 | Andjelic et al. |
| 8,932,625 B2 | 1/2015 | Hashimoto et al. |
| 2001/0038829 A1 | 4/2001 | Hasebe et al. |
| 2002/0058781 A1 | 5/2002 | Lemke |
| 2002/0131941 A1 | 9/2002 | Habeck et al. |
| 2002/0155073 A1 | 10/2002 | Fankhauser et al. |
| 2003/0165553 A1 | 9/2003 | Gers-Barlag et al. |
| 2004/0019220 A1 | 1/2004 | Fischer et al. |
| 2004/0022836 A1 | 2/2004 | Degen et al. |
| 2004/0057914 A1 | 3/2004 | Bonda et al. |
| 2004/0096406 A1 | 5/2004 | De Poilly |
| 2004/0126339 A1 | 7/2004 | Roszell |
| 2004/0197359 A1 | 10/2004 | Yamada et al. |
| 2004/0223925 A1 | 11/2004 | L'Alloret |
| 2004/0228814 A1 | 11/2004 | Didier Candau et al. |
| 2005/0031660 A1 | 2/2005 | Deckner |
| 2005/0036961 A1 | 2/2005 | Hansenne et al. |
| 2005/0048010 A1 | 3/2005 | Kliss et al. |
| 2005/0065251 A1 | 3/2005 | Didier Candau et al. |
| 2005/0180933 A1 | 8/2005 | Wei et al. |
| 2006/0045890 A1* | 3/2006 | Gonzalez ............ A61K 8/25 424/70.12 |
| 2006/0204457 A1 | 9/2006 | Toda et al. |
| 2007/0098653 A1 | 5/2007 | Tamasawa et al. |
| 2007/0134174 A1 | 6/2007 | Irwin et al. |
| 2008/0081025 A1 | 4/2008 | Poschalko et al. |
| 2008/0089852 A1 | 4/2008 | Hotz et al. |
| 2008/0247975 A1 | 10/2008 | Dueva-Koganov et al. |
| 2008/0311234 A1 | 12/2008 | Yoneda et al. |
| 2009/0016971 A1 | 1/2009 | Gaudry et al. |
| 2009/0041688 A1 | 2/2009 | Dueva-Koganov et al. |
| 2009/0068130 A1 | 3/2009 | Spaulding et al. |
| 2009/0185988 A1 | 7/2009 | Maleski et al. |
| 2009/0214460 A9 | 8/2009 | Luukas |
| 2009/0232859 A1 | 9/2009 | Sakuta et al. |
| 2009/0258230 A1 | 10/2009 | Schlossman et al. |
| 2009/0297462 A1 | 12/2009 | Hessefort et al. |
| 2009/0324523 A1 | 12/2009 | Clemente et al. |
| 2009/0324524 A1 | 12/2009 | Clemente et al. |
| 2010/0003202 A1 | 1/2010 | Matsumoto et al. |
| 2010/0008873 A1* | 1/2010 | Muller ............ A61P 17/04 424/59 |
| 2010/0129303 A1 | 5/2010 | Dueva-Koganov et al. |
| 2010/0189661 A1 | 7/2010 | Musa et al. |
| 2010/0226867 A1 | 9/2010 | Dueva-Koganov et al. |
| 2010/0239508 A1 | 9/2010 | Mori et al. |
| 2010/0284948 A1 | 11/2010 | Ohrmann et al. |
| 2011/0014139 A1 | 1/2011 | Viala et al. |
| 2011/0027202 A1 | 2/2011 | Didier Candau et al. |
| 2011/0104078 A1 | 5/2011 | Burgo et al. |
| 2011/0117034 A1 | 5/2011 | Satonaka et al. |
| 2011/0195036 A1 | 8/2011 | Clemente et al. |
| 2012/0058974 A1 | 3/2012 | Misske et al. |
| 2012/0087882 A1 | 4/2012 | Fevola et al. |
| 2012/0093753 A1 | 4/2012 | Fevola et al. |
| 2012/0282201 A1 | 11/2012 | Schlifke-Poschalko |
| 2012/0294813 A1 | 11/2012 | Frey et al. |
| 2013/0115179 A1 | 5/2013 | Janssen et al. |
| 2014/0004063 A1 | 1/2014 | Daly |
| 2014/0004064 A1 | 1/2014 | Daly |
| 2014/0127148 A1 | 5/2014 | Derain |

FOREIGN PATENT DOCUMENTS

| | | |
|---|---|---|
| EP | 413648 A | 2/1991 |
| EP | 523955 A | 1/1993 |
| EP | 601080 B | 7/1995 |
| EP | 681830 A | 11/1995 |
| EP | 1051963 A | 11/2000 |
| EP | 1291370 A | 3/2003 |
| EP | 1089986 B | 3/2005 |
| EP | 2015727 B | 1/2010 |
| EP | 2198930 A | 6/2010 |
| EP | 2679616 A | 1/2014 |
| EP | 2876126 A | 5/2015 |
| EP | 2886101 A | 6/2015 |
| FR | 2252840 A | 6/1975 |
| JP | S6099186 A | 6/1985 |
| JP | 2006-265389 A | 10/2006 |
| JP | 2009-167168 A | 7/2009 |
| RU | 2162686 C | 2/2001 |
| RU | 2009124703 | 1/2011 |
| WO | WO 1992/019214 | 11/1992 |
| WO | WO 1992/019592 A | 11/1992 |
| WO | WO 1993/022366 A | 11/1993 |
| WO | WO 1993/022413 A | 11/1993 |
| WO | WO 1996/003369 A | 2/1996 |
| WO | WO 2000/066675 A | 11/2000 |
| WO | WO 2001/008647 A | 2/2001 |
| WO | WO 2002/024668 A | 3/2002 |
| WO | WO 2002/036534 A | 5/2002 |
| WO | WO 2004/009047 A | 1/2004 |
| WO | WO 2005/092282 A | 10/2005 |
| WO | WO 2007/066309 A | 6/2007 |
| WO | WO 2007/081209 A | 7/2007 |
| WO | WO 2007/092407 A | 8/2007 |
| WO | WO 2008/056678 A | 5/2008 |
| WO | WO 2010/060776 A | 6/2010 |
| WO | WO 2010/115009 A | 10/2010 |
| WO | WO 2010/136360 A | 12/2010 |
| WO | WO 2011/003774 A | 1/2011 |
| WO | WO 2011/048570 A | 4/2011 |
| WO | WO 2011/070050 A | 6/2011 |
| WO | WO 2011/070053 A | 6/2011 |
| WO | WO 2011/070073 A | 6/2011 |
| WO | WO 2011/070075 A | 6/2011 |
| WO | WO 2011/070077 A | 6/2011 |
| WO | WO 2011/098315 A | 8/2011 |
| WO | WO 2012/129722 A | 10/2012 |
| WO | WO 2013/076691 A | 5/2013 |
| WO | WO 2014/004474 A | 1/2014 |
| WO | WO 2014/004477 A | 1/2014 |
| WO | WO 2014/149390 A | 9/2014 |
| WO | WO 2015/122770 A | 8/2015 |
| WO | WO 2017/218390 A | 12/2017 |

OTHER PUBLICATIONS

U.S. Appl. No. 13/535,890, filed Jun. 28, 2012, 2014/0004054, Jan. 2, 2014, Abandoned, Daly et al.

U.S. Appl. No. 13/710,546, filed Dec. 11, 2012, 2014/0004058, Jan. 2, 2014, Abandoned, Daly et al.

U.S. Appl. No. 14/565,968, filed Dec. 10, 2014, 2015/0086495, Mar. 26, 2015, Abandoned, Daly et al.

U.S. Appl. No. 13/535,899, filed Jun. 28, 2012, 2014/0004055, Jan. 2, 2014, Abandoned, Daly et al.

U.S. Appl. No. 13/710,555, filed Dec. 11, 2012, 2014/0004059, Jan. 2, 2014, Abandoned, Daly et al.

U.S. Appl. No. 14/566,063, filed Dec. 10, 2014, 2015/0098916, Apr. 9, 2015, Abandoned, Daly et al.

U.S. Appl. No. 13/535,909, filed Jun. 28, 2012, 2014/0004056, Jan. 2, 2014, Abandoned, Daly et al.

U.S. Appl. No. 14/132,290, filed Dec. 18, 2013, 2015/0164771, Jun. 18, 2015, Abandoned, Daly et al.

(56) References Cited

OTHER PUBLICATIONS

U.S. Appl. No. 14/674,536, filed Mar. 31, 2015, 2015/0320671, Nov. 12, 2015, Pending, Daly et al.
U.S. Appl. No. 61/991,732, filed May 12, 2014, Expired, Daly et al.
U.S. Appl. No. 62/350,863, filed Jun. 16, 2016, Expired, Daly et al.
U.S. Appl. No. 62/362,251, filed Jul. 14, 2016, Expired, Daly et al.
U.S. Appl. No. 62/378,736, filed Aug. 24, 2016, Expired, Daly et al.
U.S. Appl. No. 15/686,382, filed Aug. 25, 2017, 2018/0092819, Apr. 5, 2018, Pending, Daly et al.
U.S. Appl. No. 62/404,246, filed Oct. 5, 2016, Expired, Daly et al.
U.S. Appl. No. 13/799,193, filed Mar. 13, 2013, 2014/0004060, Jan. 2, 2014, Grant, U.S. Pat. No. 9,469,725, Oct. 18, 2016, Levins et al.
U.S. Appl. No. 61/665,430, filed Jun. 28, 2012, Expired, Levins et al.
U.S. Appl. No. 15/007,591, filed Jan. 27, 2016, 2016/0137780, May 19, 2016, Grant, U.S. Pat. No. 9,758,618, Sep. 12, 2017, Levins et al.
U.S. Appl. No. 13/799,222, filed Mar. 13, 2013, 2014/0004061, Jan. 2, 2014, Grant, U.S. Pat. No. 9,255,180, Feb. 9, 2016, Levins et al.
U.S. Appl. No. 61/665,439, filed Jun. 28, 2012, Expired, Levins et al.
Anonymous: "Personal Care Sunspheres™ Hollow Sphere Technology An APF Booster for More Aesthetically Pleasing Formulations Features, Benefits and Applications", Feb. 28, 2006 (Feb. 28, 2006), pp. 1-14, XP055321502, Retrieved from the Internet: URL:http://www.dow.com/assests/attachments/business/pcare/sunspheres/sunspheres_powder/tds/sunspheres_powder.pdf [retrieved on Nov. 22, 2016] pp. 1, 3, 6, 11.
"Crodacol™ C95 Product Details" from the Croda website, 2013 http://www.croda.com/home.aspx?view=dtl&d=content&s=157&r=401&p=2578&prodID-1779.
Erberich et al., "Polyglycidols with Two Orthogonal Protective Groups: Preparation, Selective Deprotection, and Functionalization", *Macromolecules* (2007), 40(9):3070-3079.
International search report dated Aug. 8, 2017, for international application PCT/US2017/036976.
Evans et al., "The Colloidal Domain: where physics, chemistry, biology, and technology meet," Wiley, 1999, p. 409-416; http://www.bre.orst.edu/Courses/Colloid%20Transport/documents/DLVOPrimer.pdf.
Fitton et al., "Synthesis of Simple Oxetanes Carrying Reactive 2-Substituents", *Synthesis* (1987) 1987(12):1140-1142.
Graham, A.B. et al., Inhibition of the Mitochondrial Oxidation of octanoate by Salicylic Acid and related Compounds, J. Pharm. Pharmacol. 26, pp. 531-534 (1973).
Hanson et al., "Sunscreen Enhancement of UV-induced Reactive Oxygen Species in the Skin", *Free Radical Biology & Medicine* (2006) vol. 41, pp. 1205-1212.
Haouet et al., "Preparation Et Proprietes Des Poly®-Glycidols", *European Polymer Journal* (1983), 19(12):1089-1098. (English Abstract).
Herzog et al., "Simulation of Sunscreen Perforamnce", *Pure Appl. Chem.* (2015) 87(9-10):937-951.

Im et al., "Analysis of Polymeric UV Absorber Tinuvin 213 using LDI-TOFMS: solvent effect in sample preparation", Bull. Korean Chem. Soc., Jun. 20, 2011, 32(6):2093-2096 (XP002776302).
Kuhn et al., "Monitoring the Kinetics of Ion-Dependent Protein Folding by Time-Resolved NMR Spectroscopy at Atomic Resolution", *Journal of the American Chemical Society* (2000), vol. 122, pp. 6169-6174.
Jakobson, G., Diglycerin und hoehere Oligomere des Glycerins als Synthesebausteine, Fette, Seifen Anstrichmittel, 1986, vol. 88, pp. 101-106.
Lee et al., "Poly(allyl Glycidyl Ether)—A Versatile and Functional Polyether Platform", *Journal of Polymer Science Part A: Polymer Chemistry* (2011), 49(20):4498-4504.
Li et al., "Synthesis of polyethylene glycol (PEG) derivatives and PEGylated-peptide biopolymer conjugates", *Biomacromolecules*, American Chemical Society, US, vol. 4, No. 4, May 17, 2003, pp. 1055-1067 (ISSN: 1525-7797, DOI: 10.1021/BM034069L) (XP002328259).
Lochhead, R.Y. et al., Cosmetics and Toiletries, vol. 108, pp. 95-135 (1993).
Moore et al., "Room Temperature Polyesterification", *Macromolecules* (1990), vol. 23, Issue 1, pp. 65-70.
Obermeier et al., "Poly(ethylene glycol-co-allyl glycidyl ether)s: A PEG-Based Modular Synthetic Platform for Multiple Bioconjugation", *Bioconjugate Chemistry* (2011), 22(3):436-444.
Rokicki et al., "Hyperbranched aliphatic polyethers obtained from environmentally benign monomer: glycerol carbonate", *Green Chemistry* (2005), vol. 7, pp. 529-539.
Stiriba et al., "Hyperbranched molecular nanocapsules: Comparison of the hyperbranched architecture with the perfect linear analogue", Journal of the american Chemical Society (2002) vol. 124, pp. 9698-9699.
Sunder et al., "Controlled Synthesis of Hyperbranched Polyglycerols by Ring-Opening Multibranching Polymerization", *Macromolecules* (1999), 32(13):4240-4246.
Taton et al., "Synthesis of chiral and racemic functional polymers from glycidol and thioglycidol", *Macromolecular Chemistry and Physics* (1994), 195(1):139-148.
Tchao, "Trans-Epithelial Permeability of Fluorescein In Vitro as an Assay to Determine Eye Irritants", *Alternative Methods in Toxicology 6, Progress in In Vitro Toxicology* (ed. A.M. Goldberg) (1988), pp. 271-283.
Todd, C. et al., Volatile Silicone Fluids for Cosmetic Formulations, Cosmetics and Toiletries, vol. 91, pp. 29-32 (1976).
Tokar et al., "Cationic Polymerization of Glycidol: Coexistence of the Activated Monomer and Active Chain End Mechanism", *Macromolecules* (1994), 27(2):320-322.
Tronnier, H. et al., J. Soc. Cosm. Chem. 24, pp. 281-290 (1973) (English Abstract).
Wenk, H.H. et al., Polyglycerol—A Versatile Building Block for Sustainable Cosmetic Raw Materials, SOFW—Journal, 2009, vol. 135, Issue 8, pp. 25-30.

\* cited by examiner

SUNSCREEN COMPOSITIONS CONTAINING A COMBINATION OF A LINEAR ULTRAVIOLET RADIATION-ABSORBING POLYETHER AND OTHER ULTRAVIOLET-SCREENING COMPOUNDS

CROSS-REFERENCE TO RELATED APPLICATIONS

This application is a continuation of national phase application Ser. No. 16/308,050 filed on Dec. 7, 2018 which claims the benefit of international application PCT/US2017/036976 filed on Jun. 12, 2017, which claims the benefit of U.S. provisional applications 62/350,863 filed on Jun. 16, 2016, 62/362,251 filed on Jul. 14, 2016, and 62/378,736 filed on Aug. 24, 2016, complete disclosures of which are hereby incorporated herein by reference for all purposes.

FIELD OF THE INVENTION

The present invention relates to topically-acceptable sunscreen compositions comprising a combination of linear UV-absorbing polyethers and other additional UV-screening compounds, sunscreen products made of such sunscreen compositions, and the processes of protecting keratinous substrates.

BACKGROUND OF THE INVENTION

Skin aging is the result of more than just chronological age, as skin is exposed to various environmental stresses, such as UV rays, which cause free radicals to form in the skin. The prolonged exposure to various environmental stresses such as ultraviolet (UV) radiation from the sun, can lead to the formation of free radicals in the skin and light dermatoses and erythemas, as well as increase the risk of skin cancers, such as melanoma, and accelerate skin aging, such as loss of skin elasticity and wrinkling.

Depending on the wavelength, UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation. Therefore, an effective sunscreen formulation preferably comprises both at least one UV-A and UV-B filter and a broad band UV filter covering the full range from about 290 nm to about 400 nm to prevent the human skin from the damage of sunlight.

The degree of UV protection afforded by a sunscreen composition is directly related to the amount and type of UV-screening compounds present therein. The more UV-screening compounds present, the greater the degree of UV protection.

Numerous sunscreen compositions are commercially available with varying ability to shield the body from ultraviolet light. However, numerous challenges still exist to provide sunscreen compositions that provide strong UV radiation protection. The challenge of creating sunscreens with various properties, e.g., mildness, etc., is further magnified if one imposes additional constraints on the sunscreen composition.

The present invention provides mild, aesthetic sunscreen compositions that include a combination of linear UV-absorbing polyethers and other additional UV-screening compounds.

SUMMARY OF THE INVENTION

The invention includes sunscreen compositions including a combination of a polymer composition that includes a linear ultraviolet radiation absorbing polyether that includes a covalently bound UV-chromophore, and at least one additional UV-screening compounds. Such sunscreen compositions provide unexpected synergic protection from ultraviolet radiation.

DETAILED DESCRIPTION OF THE INVENTION

Unless defined otherwise, all technical and scientific terms used herein have the same meaning as commonly understood by one of ordinary skill in the art to which the invention belongs. As used herein, unless otherwise indicated, all hydrocarbon groups (e.g., alkyl, alkenyl) groups may be straight or branched chain groups. As used herein, unless otherwise indicated, the term "molecular weight" refers to weight average molecular weight, (Mw).

Unless defined otherwise, all concentrations refer to concentrations by weight of the composition. Also, unless specifically defined otherwise, the term "essentially free of," with respect to a class of ingredients, refers to the particular ingredient(s) being present in a concentration less than is necessary for the particularly ingredient to be effective to provide the benefit or property for which it otherwise would be used, for example, about 1% or less, or about 0.5% or less.

As used herein, "UV-absorbing" refers to a material or compound, e.g. a polymeric or non-polymeric sunscreen agent or a chemical moiety, which absorbs radiation in some portion of the ultraviolet spectrum (290 nm-400 nm), such as one having an extinction coefficient of at least about 1000 $mol^{-1}$ $cm^{-1}$, for at least one wavelength within the above-defined ultraviolet spectrum. SPF values disclosed and claimed herein are determined using the in-vitro method described herein below.

Linear UV-Absorbing Polyether

Embodiments of the invention relate to compositions including a linear ultraviolet radiation absorbing polyether, (i.e., "linear UV absorbing polyether"). By linear UV absorbing polyether, it is meant a polyether that absorbs radiation in some portion of the ultraviolet spectrum (wavelengths between 290 and 400 nm). The linear UV absorbing polyether has a weight average molecular weight ($M_w$), which may be suitable for reducing or preventing the chromophore from absorbing through the skin. According to one embodiment, a suitable molecular weight for the UV absorbing polyether is $M_w$ greater than 500. In one embodiment, $M_w$ is in the range of about 500 to about 50,000. In another embodiment, the $M_w$ is in the range of about 1,000 to about 20,000, such as from about 1,000 to about 10,000.

Described herein is a composition including a linear UV-absorbing polyether. As one skilled in the art will recognize, "polyether" indicates that the UV absorbing polymer includes a plurality of ether functional groups covalently bonded to each other. The "backbone" of the linear UV-absorbing polyether refers to the longest continuous sequence of covalently bonded ether functional groups. Other smaller groups of covalently bonded atoms are considered pendant groups that branch from the backbone.

According to certain embodiments the linear UV-absorbing polyether includes glyceryl repeat units and accordingly, may be characterized as a polyglycerol. By "glyceryl repeat units" (also referred to herein "glyceryl remnant units") it is meant glycerol units excluding nucleophilic groups such as hydroxyl groups. Glyceryl remnant units include ether functional groups, and generally may be represented as $C_3H_5O$ for linear and dendritic remnants (Rokicki et al. *Green Chemistry.*, 2005, 7, 52). Suitable glyceryl remnant units include dehydrated forms (i.e. one mole of water removed) of the following glyceryl units: linear-1,4 ($L_{1,4}$) glyceryl units; linear-1,3 ($L_{1,3}$) glyceryl repeat units; dendritic (D) glyceryl units; terminal-1,2 ($T_{1,2}$) units; and terminal-1,3 ($T_{1,3}$) units. Examples of linear glyceryl remnant units and terminal units are shown below (to the right side of the arrows). The corresponding glyceryl unit before dehydration (shown to the left side of arrows; includes hydroxyls) are shown as well:

Linear-1,4 ($L_{1,4}$) Glyceryl Repeat Units

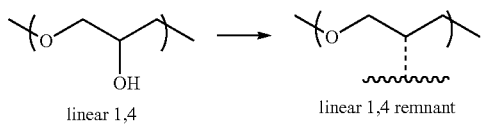

linear 1,4        linear 1,4 remnant

Linear-1,3 ($L_{1,3}$) Glyceryl Repeat Units

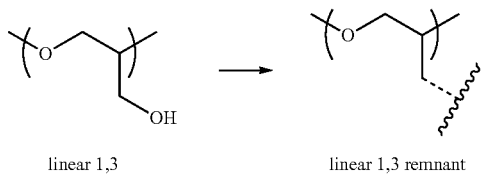

linear 1,3        linear 1,3 remnant

Terminal-1,2 ($T_{1,2}$) Units

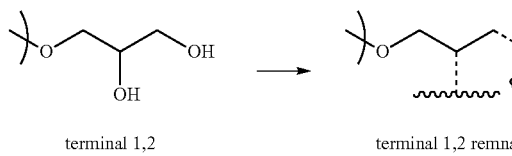

terminal 1,2        terminal 1,2 remnant

And Terminal-1,3 ($T_{1,3}$) Units

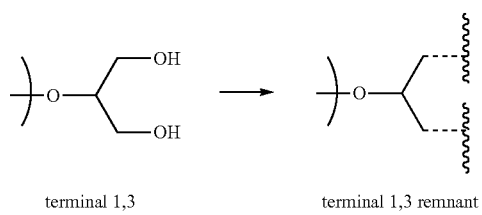

terminal 1,3        terminal 1,3 remnant

The composition includes a linear UV-absorbing polyether that comprises a covalently bound ultraviolet radiation-absorbing chromophore ("UV-chromophore"). By linear, it is meant the UV-absorbing polyether has a backbone that is unbranched.

According to certain embodiments, the linear UV-absorbing polyether includes either or both of the repeat units shown in FORMULA IA and FORMULA IIB, below:

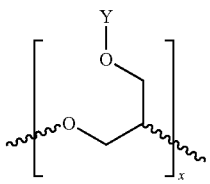

Formula IA. Repeat Unit of Linear UV-Absorbing Polyether

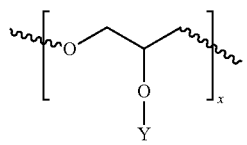

Formula IIB. Repeat Unit of Linear UV-Absorbing Polyether

In FORMULAS IA and IIB, Y represents a UV-chromophore, as described below. An illustrative example of a linear UV-absorbing polyether that comprises a covalently bound UV-chromophore is shown in FORMULA IIIC.

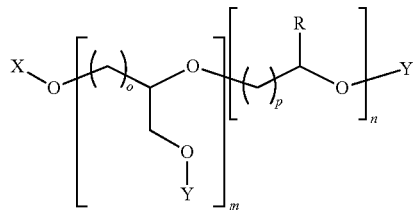

Formula IIIC. Linear UV Absorbing Polyether

In the structure illustrated in FORMULA IIIC, X is either a terminal functional group or part of the polymer backbone; R is a pendant group attached to the polymer backbone, and X is a terminal group.

X and R may either be the same or different. X and R may be independently selected from, for example, hydrogen, linear alkyl, alkenyl or alkynyl hydrocarbon chains, linear siloxanes, and the like. In one embodiment the group X represents octadecane. Y represents a UV-chromophore and the groups represented by Y are described below. The proportion of ether repeat units bearing substituent Y is a real number expressed by Equation 1, $$\frac{m}{n+m} \qquad \text{Equation 1}$$

where m and n both represent a real number between 0 and 1, and the sum of n and m equals 1. In one embodiment, the number m=1 and n=0 (the linear UV-absorbing polyether is a homopolymer and includes the repeat unit of FORMULA IA). In another embodiment, the number m<1 (the polymer is a copolymer) with R and Y pendant groups. For copolymers containing both R and Y pendant groups, the distribution of the pendant R and Y groups along the polymer chain can be modified to obtain optimal polymer properties. In one embodiment, the linear UV-absorbing polyether is a random copolymer, and the groups R and Y are statistically distributed along the polymer chain. In another embodiment, the linear UV-absorbing polyether is a block copolymer, consisting of alternating segments of polymer backbone functionalized with a greater proportion of either R or Y. In another embodiment, the distribution of the pendant groups R and Y along the polymer backbone is somewhere between the boundary conditions of block and statistically random copolymers. In FORMULA IIIC, the integers o and p represent the number of $CH_2$ groups in the repeat units bearing Y and R.

Introduction of varied R pendant groups can be achieved through the use of other co-monomers during the polymerization reaction. The size, chemical composition, weight percent and position in the backbone of these co-monomers can be varied to change the physical and chemical properties of the final UV-absorbing linear polyether. Examples of co-monomers that can be incorporated into the linear UV-absorbing polyetherinclude, but are not limited to, ethylene oxide, propylene oxide, and glycidyl ethers such as n-butyl glycidyl ether, 2-ethylhexylglycidyl ether.

It is clear to one skilled in the art that polyethers of the type illustrated in FORMULAS IA, IIB and IIIC can be obtained through various synthetic routes. Among these routes is ring-opening polymerization of cyclic ether monomers and optional co-monomers. The size of the ring in the cyclic ether monomers determines the values of o or p, and the resulting backbone structure of the linear UV-absorbing polyether. For monomers or co-monomers that are epoxides (three-membered rings containing two carbon atoms and one oxygen atom), the value of o or p in the resulting linear UV-absorbing polyether is 1. A repeat unit that results from using an epoxide co-monomer is shown in structure A of FORMULA IV. For (co)monomers that are oxetanes (four-membered rings containing three carbon atoms and one oxygen atom), the value of o or p in the resulting linear UV absorbing polyether is 2. A repeat unit that results from using an oxetane co-monomer is shown in structure B of FORMULA IV. The length of the alkyl chain within each monomer type can be selected to modify the properties of the linear UV-absorbing polyether. In one embodiment, both o and p equal 1. An example of this case is if the repeat units bearing Y and R both are derived from epoxide monomers (o=p=1), or both derived from oxetane monomers (o=p=2). In another embodiment, o and p are not equal. An example of this case is if the repeat units bearing the UV-chromophore Y are based on an epoxide monomer (o=1), and the repeat units bearing the group R are based on an oxetane monomer (p=2).

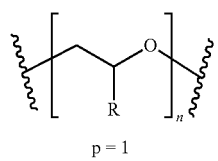

p = 1

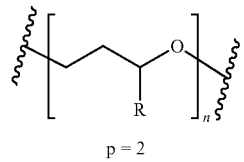

p = 2

Formula IV. Optional Repeat Units

Suitable UV-chromophores that may be covalently bound in linear UV-absorbing polyethers of the present invention include UV-absorbing triazoles (a moiety containing a five-membered heterocyclic ring with two carbon and three nitrogen atoms), such as benzotriazoles. In another embodiment, the structure represented by Y contains or has a pendant UV-absorbing triazine (a six membered heterocycle containing three nitrogen and three carbon atoms). Suitable UV-chromophores include those that have absorbance of UVA radiation. Other suitable UV-chromophores are those which have absorbance in the UVB region. In one embodiment, the UV-chromophore absorbs in both the UVA and UVB region. In one embodiment, when the linear UV-absorbing polyether is cast into a film, it is possible to generate a molar extinction coefficient measured for at least one wavelength in this wavelength range of at least about $1000\ mol^{-1}\ cm^{-1}$, preferably at least about $2000\ mol^{-1}\ cm^{-1}$, more preferably at least about $4000\ mol^{-1}\ cm^{-1}$. In one embodiment, the molar extinction coefficient among at least 40% of the wavelengths in this portion of the spectrum is at least about $1000\ mol^{-1}\ cm^{-1}$. Examples of UV-chromophores that are UVA absorbing include triazoles such as benzotriazoles, such as hydroxyphenyl-benzotriazoles; camphors such as benzylidene camphor and its derivatives (such as terephthalylidene dicamphor sulfonic acid); dibenzoyl-methanes and their derivatives.

In one embodiment, the UV-chromophore is a benzotriazole providing both photostability and strong UVA absorbance with a structure represented in FORMULA V.

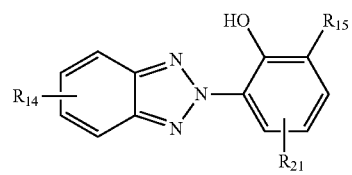

Formula V. Benzotriazole UV-Absorbing Chromophore wherein each $R_{14}$ is independently selected from the group consisting of hydrogen, $C_1$-$C_{20}$ alkyl, alkoxy, acyl, alkyloxy, alkylamino, and halogen; $R_{15}$ is independently selected from the group consisting of hydrogen, $C_1$-$C_{20}$ alkyl, alkoxy, acyl, alkyloxy, and alkylamino, $R_{21}$ is selected from $C_1$-$C_{20}$ alkyl, alkoxy, acyl, alkyloxy, and alkylamino. Either of the $R_{15}$ or $R_{21}$ groups may include functional groups that allow attachment to a polymer. Compounds resembling the structure in FORMULA V are described in U.S. Pat. No. 5,869,030, and include, but are not limited to, methylene bis-benzotriazolyl tetramethylbutylphenol (a compound sold under the trade name TINSORB M by BASF Corporation, Wyandotte, Michigan). In one embodiment, the UV-absorbing triazole is derived from a transesterification product of 3-(3-(2H-benzo[d][1,2,3]triazol-2-yl)-5-(tert-butyl)-4-hydroxyphenyl) propanoic acid with polyethylene glycol 300, commercially available as TINUVIN 213, also available from BASF. In another embodiment, the UV-absorbing triazole is Benzenepropanoic acid, 3-(2H-benzotriazol-2-yl)-5-(1, 1-dimethylethyl)-4-hydroxy-, $C_{7-9}$-branched and linear alkyl esters, commercially available as TINUVIN 99, also available from BASF. In another embodiment, the UV-absorbing group contains a triazine moiety. An exemplary triazine is 6-octyl-2-(4-(4,6-di([1,1'-biphenyl]-4-yl)-1,3,5-triazin-2-yl)-3-hydroxyphenoxy) propanoate (a compound sold under the trade name TINUVIN 479 by BASF Corporation, Wyandotte, Michigan).

In another embodiment, the UV-chromophore is a UVB-absorbing moiety. By UVB-absorbing chromophore it is meant that the UV-chromophore has absorbance in the UVB portion (290 to 320 nm) of the ultraviolet spectrum. In one embodiment, the criteria for consideration as a UVB-absorbing chromophore is similar to those described above for an UVA-absorbing chromophore, except that the wavelength range is 290 nm to 320 nm. Examples of suitable UVB-absorbing chromophores include 4-aminobenzoic acid and alkane esters thereof; anthranilic acid and alkane esters thereof; salicylic acid and alkane esters thereof, hydroxycinnamic acid alkane esters thereof, dihydroxy-, dicarboxy-, and hydroxycarboxybenzophenones and alkane ester or acid halide derivatives thereof, dihydroxy-, dicarboxy-, and hydroxycarboxychalcones and alkane ester or acid halide derivatives thereof, dihydroxy-, dicarboxy-, and hydroxycarboxycoumarins and alkane ester or acid halide derivatives thereof, benzalmalonate (benzylidene malonate); benzimidazole derivatives (such as phenyl benzilimazole sulfonic acid, PBSA), benzoxazole derivatives, and other suitably functionalized species capable of copolymerization within the polymer chain. In another embodiment, the linear UV-absorbing polyether includes more than one UV-chromophore or more than one chemical class of UV-chromophore.

The linear UV-absorbing polyethers useful in the present invention may be synthesized by, according to certain embodiments, ring-opening polymerization of a suitable cyclic ether monomer to form a polyether, followed by covalent attachment of UV-chromophores to pendant functional groups ("post-polymerization attachment"). According to certain other embodiments, the linear UV-absorbing polyethers may be synthesized by polymerization of a cyclic ether monomer, wherein the monomer itself includes a covalently attached UV-chromophore (i.e., "direct polymerization").

Furthermore, as one skilled in the art will recognize, the linear UV-absorbing polyethers that are useful in topical compositions of the present invention are prepared via polymer synthesis. Synthesis of the UV-absorbing polyether generally results in a reaction product, hereinafter referred to as a "polymer composition", that is a mixture of various molecular weights of linear UV-absorbing polyethers. The polymer composition may further include (apart from the linear UV-absorbing polyether) a small amount of unpolymerized material which may be removed using techniques known in the art. According to certain embodiments, the unpolymerized material (e.g., partially reacted or unreacted monomers or other reactants) may be partially or completely removed before inclusion in the topical compositions of the present invention, using for example, solvent extraction or supercritical $CO_2$ purification.

According to certain embodiments, the polymer composition to be incorporated into topical compositions of the present invention comprises about 50% or more of the linear UV-absorbing polyether that comprises a covalently bound UV-chromophore. According to certain other embodiments, the polymer composition comprises about 75% or more of the linear UV-absorbing polyether that comprises a covalently bound UV-chromophore. According to certain other embodiments, the sunscreen composition comprises about 90% or more of the linear UV-absorbing polyether, such as about 95% or more.

According to certain embodiments, the sunscreen composition has a low polydispersity. For example, the polydispersity index of the polymer composition may be about 1.5 or less, such as about 1.2 or less. Polydispersity index is defined as $M_w/M_N$ (i.e., the ratio of weight average molecular weight, $M_w$, to number average molecular weight, $M_N$). According to certain other embodiments, the polymer composition includes 50% or more by weight of a particular linear UV-absorbing polyether molecule.

Polydispersity of the polymer composition may be kept low using, for example, particular synthetic procedures, such as ring-opening polymerization of a cyclic ether monomer and deprotection (described below). Alternatively, or in addition, the polymer composition may be treated using techniques known in the art, such as supercritical $CO_2$ to purify the polymer composition (e.g., before or after attachment of UV-chromophore).

Synthesis of the linear, UV-absorbing polyether by post-polymerization attachment of the UV-chromophore may include the steps of ring-opening polymerization of a cyclic ether monomer to form a polyether having protected groups; deprotecting the polyether to remove at least some of the protected groups; and attaching a UV-chromophore to the deprotected linear UV-absorbing polyether to form a linear UV-absorbing polyether having a covalently bound UV chromophore.

An example of forming the linear, UV-absorbing polyether post-polymerization attachment is illustrated schematically in FORMULA VI. An initiator I is used to induce polymerization of cyclic ether monomer M, generating polymer $P_0$ wherein pendant hydroxy functional groups are protected with a protecting group (P). Polymer $P_0$ is subjected to conditions that remove protecting group P, affording deprotected polymer $P_d$. Finally, UV-chromophore Y is attached to the pendant hydroxyl groups of polymer $P_d$, affording the desired final polymer, $P_f$.

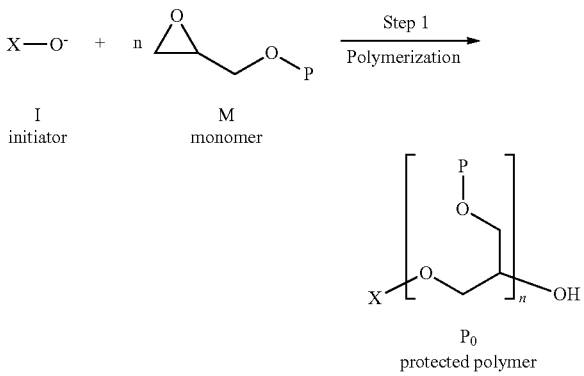

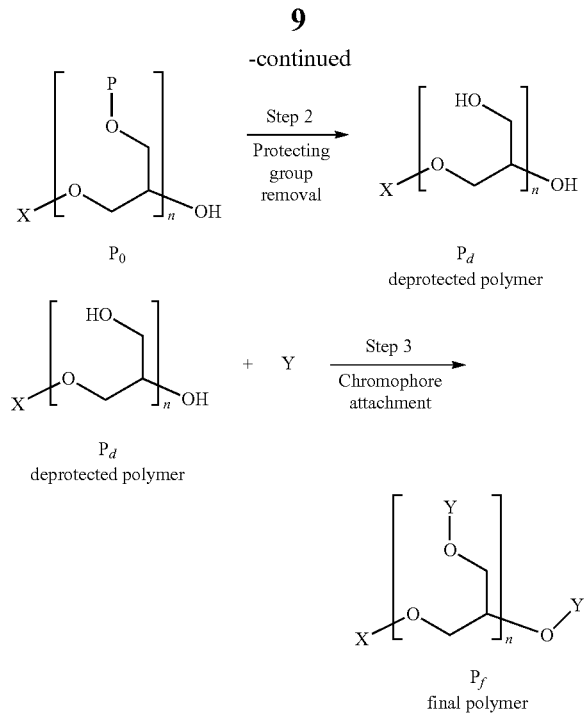

Formula VI. Synthesis of UV-Absorbing Chromophore by Post-Polymerization Functionalization Ring-opening polymerization of cyclic ethers such as monomer M in FORMULA VI can be achieved using various methods including cationic and anionic ring-opening polymerization. In one embodiment, the polymerization is performed by anionic ring opening polymerization. Monomer M in FORMULA VI is a form of glycidol wherein the primary hydroxy group has been masked with protecting group P. Polymerization of unprotected glycidol results in the formation of highly branched polymers (U.S. Pat. No. 7,988,953B2, Tokar, R. et. al. *Macromolecules* 1994, 27, 320-322: Sunder, A. et. al. *Macromolecules* 1999: 4240-4246. Rokicki, G. et. al. *Green Chemistry* 2005, 7, 529). Conversely, anionic polymerization of glycidol derivaties where the primary hydroxyl group has been protected can generate linear polyethers, as illustrated by structure $P_0$ in FORMULA VI (Taton, D. et. al. *Macromolecular Chemistry and Physics* 1994, 195, 139-148: Erberich, M. et. al. *Macromolecules* 2007, 40, 3070-3079: Haouet, A. et. al. *European Polymer Journal* 1983, 19, 1089-1098: Obermeier, B. et. al *Bioconjugate Chemistry* 2011, 22, 436-444: Lee, B. F. et. al. *Journal of polymer science. PartA, Polymer chemistry* 2011, 49, 4498-4504). The protected cyclic ether monomer is not limited to epoxide derivates, and includes functionalized cyclic ethers containing 3 through 6 contiguous atoms; in another embodiment, the monomer M is an oxetane derivative containing a protected primary hydroxyl group.

By protected, it is meant that a functional group in a multifunctional molecule has been selectively derivatized with a moiety that prevents covalent modification at that functional group. Moieties that are used as protecting groups are typically attached to the desired functional groups with excellent chemical yield, and can be selectively removed as required in good yield, revealing the original functional group. Hydroxyl protecting groups include but are not limited to ethers such as methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), t-butoxymethyl, 4-pentenyloxymethyl (POM), siloxymethyl, 2-methoxyethoxymethyl (MEM), 2,2,2-trichloroethoxymethyl, bis(2-chloroethoxy) methyl, 2-(trimethylsilyl)ethoxymethyl (SEMOR), tetrahydropyranyl (THP), allyl, 3-bromotetrahydropyranyl, tetrahydrothiopyranyl, 1-methoxycyclohexyl, benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, trimethylsilyl (TMS), triethylsilyl (TES), trii sopropylsilyl (TIPS), t-butyldimethylsilyl (TBDMS), t-butyldiphenylsilyl (TBDPS), tribenzylsilyl, esters such as formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), and carbonates such as alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate. In one embodiment, the protecting group is ethoxyethyl ether; in another embodiment, the protecting group is allyl ether.

Removal of protecting groups from the protected linear polyether $P_0$ to generate deprotected polymer $P_d$ is achieved using methods complimentary to the choice of protecting group P; such methods are familiar to those skilled in the art. In one embodiment, the primary hydroxyl group of the cyclic ether monomer is protected as the 1-ethoxyethyl ether; the cleavage of this protecting group to generate the deprotected polymer is achieved using aqueous acidic conditions such as aqueous acetic acid, aqueous hydrochloric acid, or acidic ion exchange resin. In another embodiment, the primary hydroxyl group of the cyclic ether monomer protected as an allyl ether; the cleavage of this protecting group to generate the deprotected polymer is achieved by isomerizaion of the allyl ether to the vinyl ether by treatment with potassium alkoxide followed by treatment with aqueous acid, isomerization using transition metal catalysts followed by acidic hydrolysis, or direct removal using palladium (0) catalysts and a nucleophilic scavenger.

The anionic ring-opening polymerization of monomer M illustrated in FORMULA VI is initiated by alkoxide salt I. Examples of alkoxides suitable for initiation of ring-opening polymerization of cyclic ether monomers include, but are not limited to the potassium salts of linear $C_3$ through $C_{30}$ hydrocarbon alcohols, polyethylene glycol methyl ether, and carbinol terminated polysiloxanes. In one embodiment, the initiator for anionic ring-opening polymerization is the potassium salt of octadecanol. Another embodiment of the current invention makes use of a multifunctional initiator including, but not limited to polyoxyalkylenes such as polyethylene glycol, polypropylene glycol or poly(tetramethylene ether) glycol; polyesters such as poly(ethyleneadipate), poly(ethylenesuccinate); copolymers that have both oxyalkylene and ester functionality in the backbone such as poly[di(ethylene glycol)adipate]; and lower molecular weight alcohols such as 1,4-butanediol, 1,6-hexanediol or neopentyl glycol.

Depending on the functional groups pendant from the polyether, chromophores can be covalently attached to the polymer backbone using a variety of methods known to those skilled in the art. The following methods are illustrative, and do not represent an exhaustive list of the possible means to attach a UV-chromophore to the polymer backbone. In the case of polymers with free hydroxyl groups (as represented by structure $P_d$ in FORMULA VI) a UV-chromophore containing a carboxylate group may be covalently attached to the polymer using a number of methods familiar to those skilled in the art. Condensation reagents can be used to form covalent bonds between UV-chromophores with carboxylic acids and hydroxyl groups on polymers generating ester bonds; in one embodiment, the condensation reagent is N-(3-dimethylaminopropyl)-N'-ethylcarbodiimide hydrochloride. The carboxylic acid of the UV-chromophore may also be attached to hydroxyl groups on the polymer through ester bonds using transition metal catalysis; in one embodiment, the catalyst is tin (II) ethylhexanoate. The UV-chromophore can also be attached to the polymer by converting the carboxylic acid of the UV-chromophore to the corresponding acid chloride; the acid chloride reacts with hydroxyl groups on the functional polymer forming ester bonds; in one embodiment, this conversion to the acid chloride is performed using thionyl chloride. The UV-chromophore carboxylic acid may also be converted to the isocyanate through Curtius rearrangement of an intermediate acid azide; the chromophore isocyanate reacts with hydroxyl groups on the functional polymer forming a urethane bonds. In another embodiment, the carboxylic acid on the UV-chromophore can be converted to an ester, and attached to the hydroxyl group on the backbone by transesterification. This can be achieved by conversion of the carboxylic acid to an ester with a low boiling alcohol such as methanol; transesterification is performed by reacting the chromophore ester with the polymer containing side chain hydroxyl groups using an acid catalyst, for instance, para-toluene sulfonic acid.

Also in the case of polyethers with free hydroxyl groups, a UV-chromophore containing a hydroxyl group may be covalently attached to the polyether using a number of methods familiar to those skilled in the art. In one embodiment, the hydroxyl group on the UV-chromophore can be activated for nucleophilic displacement using a reagent such as methane sulfonyl chloride or p-toluene sulfonyl chloride; the hydroxyl groups on the backbone are then able to displace the resulting mesylate or tosylate under basic conditions to generate an ether bond between the polymer and the UV-chromophore. In another embodiment, the hydroxyl group on the UV-chromophore can be converted to the chloroformate using a reagent such as phosgene, diphosgene, or triphosgene; the resulting UV-chromophore chloroformate can react with hydroxyl groups on the backbone of the polymer to generate a carbonate bond between the polymer and the UV-chromophore. In the case of polymers with free hydroxyl groups (as represented by structure $P_d$ in FORMULA VI) a UV-chromophore containing an amine group may be covalently attached to the polymer using a number of methods familiar to those skilled in the art. In one embodiment, the hydroxyl groups on the polymer can be converted to the corresponding chloroformates using a reagent such as phosgene, diphosgene and triphosgene; the amine functionalized UV-chromophore can then react with the polymer chloroformates generating a carbamate bond between the UV-chromophore and polyether.

In another embodiment, some of the hydroxyl groups on the linear polyether backbone remain after the acid, acid chloride or isocyanate functional UV-chromophores are attached. These unreacted hydroxyl groups may be used to attach other monofunctional side groups to improve the physical and chemical properties of the polymer. Examples of hydroxyl reactive functional groups include, but are not limited to, acid chlorides and isocyanates. Specific examples of hydroxyl reactive functional side groups include palmitoyl chloride and stearyl isocyanate. Other examples of groups that may be pendant from polymers that are sites for covalent attachment of UV-chromophores include, but are not limited to, conjugated alkenes, amines, and carboxylic acids.

In a another embodiment, the polyether backbone is a polyglycerol with pendant hydroxyl groups or hydrophobic groups, such as a polyglyceryl ester, for example, decaglyceryl monostearate sold under the tradename POLYALDO 10-1-S by Lonza in Allendale, NJ or tetradecaglyceryl monostearate sold under the tradename POLYALDO 14-1-S by Lonza in Allendale, NJ The pendant hydroxyl groups may be reacted with a UV-chromophore containing a complementary functional group as described above to obtain a linear UV absorbing polyether. In this embodiment, the polymer composition will be, for example, the reaction product of a polyglycerol ester and a UV chromophore having a functional group suitable for covalent attachment to said polyglycerol ester. Suitable functional groups on the UV chromophore include carboxylates, isocyanates, among other functional groups discussed previously. The resulting polymer composition may include a linear UV-absorbing polyether having the repeat unit shown in FORMULA IIB. The resulting polymer composition may further include some non-linear (e.g., cyclic components) as well, depending upon the percentage of linear material present in the polyglycerol.

As described above, the synthesis of suitable polymer compositions containing the linear UV-absorbing polyethers can also be achieved through polymerization of UV-chromophores covalently modified with cyclic ether groups (direct polymerization). This is illustrated in FORMULA VII, where Y represents a UV-chromophore, and o is a characteristic of the ring size of the cyclic ether monomer.

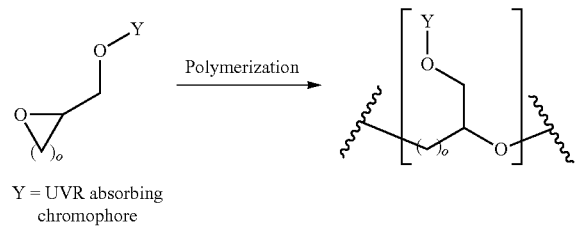

Y = UVR absorbing chromophore

Formula VII. Direct Polymerization of UV-Chromophore Covalently Attached to Cyclic Ether Additional UV-Screening Compounds The sunscreen compositions of the present invention further include at least one additional UV screening compounds. Additional UV screening compounds may be classified according to the type of protection they provide as UV-absorbing compounds or UV blocking compounds.

One type of additional UV-screening compounds that the sunscreen composition may include UV-absorbing compounds. Such UV-absorbing compounds that the sunscreen composition includes may be characterized as "organic" sun filters. The "organic" UV-absorbing compounds, often referred to as "monomeric, organic UV-absorbers" are generally aromatic compounds conjugated with a carbonyl moiety substituted in the ortho- or para-position of the aromatic ring.

Traditional organic sun filters are aromatic, small molecules, with molecular weight values <900 g/mol. Example of "organic" non-polymeric UV-absorbing compounds include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, trolamine salicylate, and homosalate; sulfonic acid derivatives such as phenylbenzimidazole sulfonic acid; benzone derivatives such as dioxybenzone, sulisobenzone, and oxybenzone; benzoic acid derivatives such as aminobenzoic acid and octyldimethyl para-amino benzoic acid; octocrylene and other $\beta,\beta$-diphenylacrylates; dioctyl butamido triazone; octyl triazone; butyl methoxydibenzoylmethane; drometrizole trisiloxane; and menthyl anthranilate.

Preferably, organic" UV-absorbing compounds include avobenzone, oxybenzone, octocrylene, salicylate derivatives (homosalate and ethylhexyl salicylate), cinnamate derivatives (octyl methoxycinnamate [OMC]), triazone derivatives (Uvinul T150 [ethylhexyl triazone]; UVASorb HEB [diethylhexyl butamido triazone]; Tinosorb S [bis-ethylhexyloxyphenol methoxyphenyl triazine]), benzoate derivatives (Uvinul A Plus [diethylamino hydroxybenzoyl hexyl benzoate]), benzotriazole derivative (Mexoryl XL [drometrizole trisiloxane]), and camphor derivatives (Mexoryl SX [ecamsule]; terephthalylidene dicamphor sulfonic acid). Anthranilate derivatives (like meradimate) are less commonly used filters because of low efficacy.

Avobenzone (a dibenzoylmethane derivative) is one of the most efficient UVA-absorbing filters used around the globe, and it is the only UVA-absorbing organic sun filter approved in the US. However, avobenzone is prone to photo instability because of an enol-to-keto tautomerization as shown in FIGURE X.1 (Kockler et al. 2012). The enol form of avobenzone absorbs in the UVA (315-400 nm), while the diketo form absorbs in the UVC (200-280 nm) and is prone to degradation (Kockler et al. 2012). Other photostabilizing ingredients must be used in combination with avobenzone to prevent light-induced degradation (Cole et al. 2009). In order to achieve photostability of avobenzone, it must be combined with ingredients that are efficient in both triplet quenching as well as singlet quenching. Examples of triplet quenchers are the following UV filters: octocrylene, 4-methylbenzylidene camphor (ex-US), Tinosorb S (ex-US) or emollients such as diethylhexyl-2,6-naphthalate (Cole et al. 2009). In addition, higher levels of oxybenzone are known to stabilize avobenzone by the singlet quenching mechanism (Cole et al. 2009). A combination of singlet and triplet quechers is most efficient in stabilizing avobenzone.

Cinnamates are very efficient UVB absorbers, but also have issues with photostabliity. OMC is a member of the cinnamate class that is known to react with avobenzone to produce non-UV light absorbing photoproducts. Hence, combinations of avobenzone and OMC are unfavorable and should be avoided because of enhanced photo instability (Cole et al. 2009; Ou-Yang et al. 2010).

Salicylate derivatives are photostable, UVB-absorbing filters that have a long history of usage. They are excellent solubilizers for crystalline UV filters, including oxybenzone and avobenzone. The absorption efficiency of these filters is quite low, however.

Oxybenzone (a benzophenone derivative) is used in many US sunscreen formulations with absorbance in the UVB (290-320 nm) and the UVA II region (320-340 nm). Padimate O is a derivative of para-aminobenzoic acid that is a liquid and is oil-soluble. It is a very effective UVB filter with one of the highest molar extinction coefficients of the approved filters. It is not widely used in products over concern that the parent molecule, para-aminobenzoic acid, has been associated with allergic reactions. Octocrylene is another oil-soluble UVB filter that has been widely used to provide increased sun protection factor (SPF) values and to also boost the photostability of avobenzone when used in combination. Ensulizole (phenylbenzimidazole sulfonic acid) is a water-soluble filter and is used in products formulated to feel lighter and less oily, such as daily-use cosmetic moisturizers. Currently, it is not permitted to be combined with avobenzone in the US and must rely on other UVA absorbers (such as zinc oxide) to provide broad-spectrum protection.

Additional examples of "organic" UV-absorbing compounds include, but are not limited to: Bis-Ethylhexyloxyphenol Methoxyphenyl Triazine; Butyl Methoxydibenzoylmethane; Diethylhexyl Butamido Triazone; Ethylhexyl Triazone; Diethylamino Hydroxy Benzoyl Hexyl Benzoate; Ethylhexyl Methoxycinnamate; Ethylhexyl Salicylate; Homosalate; Octocrylene; Methylene Bis-Benzotriazolyl Tetramethylbutylphenol; Phenylbenzimidazole Sulfonic Acid; (2-{4-[2-(4-Diethylamino-2-hydroxy-benzoyl)-benzoyl]-piperazine-1-carbonyl}-phenyl)-(4-diethylamino-2-hydroxy-phenyl)-methanone; BBDAPT; Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino] bis-, dibutyl ester; benzylidene malonates; and merocyanine derivatives; Bis(butylbenzoate) diaminotriazine aminopropylsiloxane; Bis-Ethylhexyloxyphenol Methoxyphenyl Triazine) encapsulated in a polymer matrix; 2-(2H-Benzotriazol-2-yl)-6-[(2-ethylhexyloxy)methyl]-4-methylphenol; and 2-Propenoic acid, 3-(4-methoxyphenyl)-, 2-methylphenyl ester.

Further examples of "organic" UV-absorbing compounds include, but are not limited to: Bis-Ethylhexyloxyphenol Methoxyphenyl TriazineButyl Methoxydibenzoylmethane; Diethylhexyl Butamido Triazone; Ethylhexyl Triazone; Diethylamino Hydroxy Benzoyl Hexyl Benzoate; Ethylhexyl Methoxycinnamate; Ethylhexyl Salicylate; Homosalate; Octocrylene; Methylene Bis-Benzotriazolyl Tetramethylbutylphenol; Phenylbenzimidazole Sulfonic Acid; Tris-Biphenyl Triazine; (2-{4-[2-(4-Diethylamino-2-hydroxy-benzoyl)-benzoyl]-piperazine-1-carbonyl}-phenyl)-(4-diethylamino-2-hydroxy-phenyl)-methanone; merocyanine derivatives; Bis(butylbenzoate) diaminotriazine aminopropylsiloxane; and Bis-Ethylhexyloxyphenol Methoxyphenyl Triazine, encapsulated in a polymer matrix.

In certain embodiment of the invention, the "organic" UV-absorbing compounds are selected from Table 1. (From the Daly Book Chapter)

TABLE 1

List of sun filters approved in the US, Canada, European Union, ASEAN, and MERCOSUR; alternate names; and approved usage levels per region.

| Filter name | Other names | Coverage | Maximum allowed concentration (%) | | | | | |
| --- | --- | --- | --- | --- | --- | --- | --- | --- |
| | | | US | Canada | EU | MERCOSUR | Australia | ASEAN |
| Benzophenone-3 | Oxybenzone or 2-hydroxy-4-methoxybenzophenone | UVA/B | 6 | 6 | 10 | 10 | 10 | 10 |
| Benzophenone-4 | Sulizobenzone or 2-hydroxy-4-methoxybenzophenone-5-sulfonic acid and its trihydrate | UVA/B | 10 | 10 | 5 | 10 (of acid) | 10 | 5 |
| Benzophenone-5 | 2-hydroxy-4-methoxybenzophenone-5-sulfonic acid (benzophenone-5) and its sodium salt Sulizobenzone sodium Sodium hydroxymethoxybenzophenone sulfonate | UVA/B | — | — | 5 | 5% (expressed as acid) | 10 | — |
| Benzophenone-8 | Dioxybenzone or 2,2'-dihydroxy-4-methoxybenzophenone dioxybenzone (2-hydroxy-4-methoxyphenyl)(2-hydroxyphenyl)methanone methanone, (2-hydroxy-4-methoxyphenyl)(2-hydroxyphenyl) | UVA/B | 3 | 3 | — | 3 | 3 | — |
| 3-benzylidene camphor | 3-benzylidene camphor | UVB | — | — | 2 | 2 | — | 2 |
| Bis ethylhexyloxyphenol methoxyphenyl triazine | Tinosorb S or (1,3,5)-triazine-2,4-bis{[4-(2-ethyl-hexyloxy)-2-hydroxy]-phenyl}-6-(4-methoxyphenyl) or anisotriazine | UVA/B | — | — | 10 | 10 | 10 | 10 |
| Butylmethoxy dibenzoyl methane | Avobenzone or 1-(4-tert-butylphenyl)-3-(4-methoxyphenyl) propane-1,3-dione | UVA | 3 | 5 | 5 | 5 | 5 | 5 |
| Camphor benzalkonium methosulfate | Mexoryl SO or N,N,N-trimethyl-4-(2-oxoborn-3-ylidene-methyl) anilinium methyl sulphate | UVB | — | — | 6 | 6 | 6 | 6 |
| Diethylamino hydroxybenzoyl hexyl benzoate | Uvinul A plus or benzoic acid, 2-[4-(diethylamino)-2-hydroxybenzoyl]-, hexylester | UVA | — | — | 10 | 10 | — | — |
| Diethylhexyl butamido triazone | UVASorb HEB or benzoic acid, 4,4-((6-((4-(((1,1-dimethylethyl) amino) carbonyl) phenyl) amino) 1,3,5-triazine-2,4-diyl) diimino) bis -(2-) ester) or dioctyl butamido triazone | UVB | — | — | 10 | 10 | — | 10 |
| Disodium phenyl dibenzimidazole tetrasulfonate | Neo Heliopan AP or monosodium salt of 2-2'-bis(1,4-phenylene)1H-benzimidazole-4,6-disulphonic acid) or bisimidazylate | UVA | — | — | 10 | 10% (expressed as acid) | 10 | 10 |
| Drometrizole trisiloxane | Mexoryl XL or phenol,2-(2H-benzotriazol-2-yl)-4-methyl-6-(2-methyl-3-(1,3,3,3-tetramethyl-I-(trimethylsilyl)oxy)-disiloxanyl)propyl) | UVA/B | — | — | 15 | 15 | 15 | 15 |
| Ethoxyethyl methoxycinnamate | Cinoxate | UVB | 3 | 3 | — | 3 | — | 10 |
| Ethylhexyl dimethylamino Benzoate | Padimate O Octyl dimethyl PABA Ethylhexyl dimethyl PABA | UVB | 8 | 8 | 8 | 8 | — | 8 |
| Ethylhexyl methoxycinnamate | OMC or octinoxate Octyl methoxycinnamate | UVB | 7.5 | 8.5 | 10 | 10 | 10 | 10 |
| Ethylhexyl salicylate | Octisalate 2-ethylhexyl salicylate Octyl salicylate | UVB | 5 | 6 | 5 | 5 | 5 | 5 |
| Ethylhexyl triazone | Uvinul T150 2,4,6-trianilino-(p-carbo-2'-ethylhexyl-l'oxy)-1,3,5-triazine Octyl triazone | UVB | — | — | 5 | 5 | 5 | — |
| Homosalate | 3,3,5-trimethylcyclohexyl 2-hydroxybenzoate Salicilato de homomentila | UVB | 15 | 15 | 10 | 15 | 15 | 10 |

TABLE 1-continued

List of sun filters approved in the US, Canada, European Union, ASEAN, and MERCOSUR; alternate names; and approved usage levels per region.

| | | | Maximum allowed concentration (%) | | | | | |
|---|---|---|---|---|---|---|---|---|
| Filter name | Other names | Coverage | US | Canada | EU | MERCOSUR | Australia | ASEAN |
| Isoamyl p-methoxycinnamate | Amiloxate Isopentyl-4-methoxycinnamate | UVB | — | — | 10 | 10 | 10 | 10 |
| Methyl anthranilate | Meradimate | UVA | 5 | 5 | — | 5 | 5 | 5 |
| 4-methylbenzylidene camphor | Enzacamene 3-(4'-methylbenxylidene)d-1 camphor 4 MBC | UVB | — | 6 | 4 | 4 | 4 | 4 |
| Methylene bis-benzotriazolyl tetramethylbutylphenol | Tinosorb M 2,2'-methylene-bis-6-(2H-benzotriazol-2yl)-4-(tetramethyl-butyl)-1,1,3,3-phenol | UVA/B | — | — | 10 | 10 | 10 | 10 |
| Octocrylene | 2-cyano-3,3-diphenyl acrylic acid, 2-ethylhexyl ester | UVB | 10 | 12 | 10 | 10 (of acid) | 10 | 10 |
| Para aminobenzoic acid | PABA 4-aminobenzoic acid | UVB | 15 | 15 | 5 | 15 | 15 | — |
| PEG-25 PABA | Ethoxylated ethyl-4-aminobenzoate | UVB | — | — | 10 | 10 | 10 | 10 |
| Phenyl benzimidazole sulfonic acid | Neo Heliopan Hydro-Ensulizole 2-phenylbenzimidazole-5-sulphonic acid and its potassium, sodium, and triethanolamine salts Potassium, Sodium, and TEA Phenylbenzimidazole sulfonate | UVB | 4 | 8 | 8 | 8 (as acid) | 4 | 8 |
| Polyacrylamido methylbenzylidene Camphor | Mexoryl SW Polymer of N-[(2 and 4)-[(2-oxoborn-3-ylidene)methyl]benzyl]acrylamide | UVB | — | — | 6 | 6 | — | 6 |
| Polysilicone-15 | Parsol SLX Diethylbenzylidene malonate Dimethicone Diethylmalonylbenzylidene Oxypropene dimethicone Dimethicodiethylbenzalmalonate | UVB | — | — | 10 | 10 | 10 | 10 |
| Triethanolamine salicylate | Neo Heliopan TES Trolamine salicylate | UVB | 12 | 12 | — | 12 | 12 | 12 |
| Terephtalydene dicamphor sulfonic acid | Mexoryl SX | UVA | — | — | 10 | 10 ( expressed as acid) | 10 | 10 |
| Benzylidene camphor sulfonic acid | Alpha-(2-oxoborn-3-ylidene)-toluene-4-sulfonic acid and its salts | | — | — | 6 | 6% (expressed as acid) | 6 | 6 |
| Titanium dioxide | | UVA/B | 25 | 25 | 25 | 25 | 25 | 25 |
| Zinc oxide | | UVA/B | 25 | 20 | 20 | 25 | 20 | 25 |

ASEAN, Association of Southeast Asian Nations; EU, European Union; MBC, methylbenzylidene camphor; MERCOSUR, Southern Common Market, consisting of Argentina, Brazil, Paraguay, Uruguay, and Venezuela; OMC, octyl methoxycinnamate; PABA, para-aminobenzoic acid; US, United States; UVA, ultraviolet A; UVB, ultraviolet B.

Another type of the Organic UV absorbing compounds is polymeric made of organic chromophores attached to a polysiloxane chain approved for use outside North America. The average molecular weight is >6000 daltons, so it is envisioned that the molecule is large enough to reduce permeation through the skin, making it ideal for mild applications. The polysiloxane backbone not only links the chromophores together, but it also provides a pleasant aesthetic to skin or hair. Examples of polysiloxane UV-absorbing compounds include, without limitation to, Parsol SLX and polysilicone-15. Such polysiloxane UV-absorbing compounds absorb in the UVB ($\lambda$max=312 nm) part of the spectrum and are typically combined with UVA filters to achieve broad-spectrum protection.

Yet another type of additional UV-screening compounds that the composition may include is ultraviolet-blocking compounds. UV blocking compounds reflect, absorb or scatter the UV radiation and if present in sun screen formulations, can reflect all the ultraviolet, visible and infrared rays that enhance sun protection. UV blockers are inorganic metallic oxides, including titanium dioxide, zinc oxide, and certain other transition metal oxides. Such ultraviolet blocking compounds are typically solid particles in their micronized and nanonized forms having a diameter from about 0.1 micron to about 10 microns.

Preference is given to the following UV filters:
Diethylamino Hydroxybenzoyl Hexyl Benzoate,
Ethylhexyl Triazone,
Bis-Ethylhexyloxyphenol Methoxyphenyl Triazine,
Methylene Bis-Benzotriazolyl Tetramethylbutylphenol,
Bis-Ethylhexyloxyphenol Methoxyphenyl Triazine encapsulated in a polymer matrix,
Tris-Biphenyl Triazine,
Ethylhexyl Methoxycinnamate,
Octocrylene,
1,1'-(1,4-piperazinediyl)bis[1-[2-[4-(diethylamino)-2-hydroxybenzoyl]phenyl]-methanone Titanium dioxide,
Phenylbenzimidazole Sulfonic Acid, Zinc oxide,
Ethylhexyl salicylate,
Homosalate,
Diethylhexyl butamido triazone,
Isoamyl p-methoxycinnamate,
Polysilicone-15,
Highly preferred are:
Diethylamino Hydroxybenzoyl Hexyl Benzoate,
Ethylhexyl Triazone,
Bis-Ethylhexyloxyphenol Methoxyphenyl Triazine,
Methylene Bis-Benzotriazolyl Tetramethylbutylphenol,
Bis-Ethylhexyloxyphenol Methoxyphenyl Triazine encapsulated in a polymer matrix,
Tris-Biphenyl Triazine,
Ethylhexyl Methoxycinnamate,
Octocrylene, and
1,1'-(1,4-piperazinediyl)bis[1-[2-[4-(diethylamino)-2-hydroxybenzoyl]phenyl]-methanone.

In one embodiment of the present invention, the additional UV-absorbing compound is avobenzone.

Topical Sunscreen Composition

The sunscreen compositions described herein are useful in applications where UV absorption is desired. For example, the sunscreen composition may be useful for combining with a suitable cosmetically acceptable carrier for cosmetic applications or combining the sunscreen composition with other materials to reduce UV degradation of the materials (i.e., melt blending the material with the polymer composition or coating the material with the polymer composition). The incorporation of linear UV-absorbing polyethers into such compositions of the present invention may provide enhanced SPF (primarily UVB absorbance), enhanced PFA (primarily UVA absorbance) or enhancement of both. The cosmetically-acceptable topical carrier is suitable for topical application to human skin and may include for example, one or more of vehicles such as water, ethanol, isopropanol, emollients, humectants, and/or one or more of surfactants/emulsifiers, fragrances, preservatives, water-proofing polymers, and similar ingredients commonly used in cosmetic formulations. As such, the sunscreen composition may be formulated using ingredients known in the art into a spray, lotion, gel, stick or other product forms. Similarly, according to certain embodiments, one may protect human skin from UV radiation by topically applying a composition comprising the sunscreen composition containing a combination of the linear UV-absorbing polyether and other additional UV-screening compounds According to certain other embodiments, the sunscreen composition may include additional UV-absorbing polymers, other than the linear UV-absorbing polyethers, as defined herein, and/or non-UV-absorbing, light-scattering particles. Additional UV-absorbing polymers are molecules that can be represented as having one or more structural units that repeat periodically, e.g., at least twice, to generate the molecule, and may be UV-absorbing polyethers, other than those used in compositions as defined and claimed in this specification.

Additional UV-absorbing polymers may have a molecular weight of greater than about 1500. Examples of suitable additional UV-absorbing polymers include benzylidene malonate silicone, including those described in U.S. Pat. No. 6,193,959, to Bernasconi et al. A particularly suitable benzylidene malonate includes "Parsol SLX," commercially available from DSM (Royal DSM N.V.) of Heerlen, Netherlands. Other suitable additional UV-absorbing polymers are disclosed in U.S. Pat. Nos. 6,962,692; 6,899,866; and/or U.S. Pat. No. 6,800,274; including hexanedioic acid, polymer with 2,2-dimethyl-1,3-propanediol, 3-[(2-cyano-1-oxo-3,3-diphenyl-2-propenyl)oxy]-2,2-dimethylpropyl 2-octyldodecyl ester; sold under the trade name "POLYCRYLENE," commercially available from the Hall-Star Company of Chicago, Illinois When utilized, such additional UV-absorbing polymers may be used at concentrations of about 1% or more, for example about 3% or more.

Non-UV-absorbing, light-scattering particles do not absorb in the UV spectrum, but may enhance SPF by scattering of the incident UV radiation. Examples of non-UV-absorbing, light-scattering particles include solid particles having a dimension, e.g., average diameter, from about 0.1 micron to about 10 microns. In certain embodiments, the non-UV-absorbing, light-scattering particle is a hollow particle comprising, or consisting essentially of, an organic polymer or a glass. Suitable organic polymers include acrylic polymers, including acrylic/styrene copolymers, such as those known as SUNSPHERES, which are commercially available from Dow Chemical of Midland, Michigan Suitable glasses include borosilicate glasses such as those described in published United States Patent Application US20050036961A1, entitled, "AESTHETICALLY AND SPF IMPROVED UV-SUNSCREENS COMPRISING GLASS MICROSPHERES".

In one embodiment, a composition suitable for topical/cosmetic use for application to the human body, e.g., keratinaceous surfaces such as the skin, hair, lips, or nails, and especially the skin, is provided. The sunscreen composition includes a combination of the polymer composition comprising the one or more linear UV-absorbing polyethers that comprise a covalently bound UV-chromophore and at least one additional UV-screening compounds.

The concentration of the UV-absorbing polyether may vary from about 1% to about 30%, such as from about 2% to about 20%, such as from about 5% to about 15% of the topical sunscreen composition. In certain embodiments, the concentration of UV-absorbing polyether is about 2% or more, such as about 5% or more, such about 15% or more of the sunscreen composition.

The concentration of the additional UV-screening compounds in the topical sunscreen composition may vary from about 1% to about 40%, such as from about 2% to about 30%, such as from about 50% to about 20% of the topical composition. In certain embodiments, the concentration of additional UV-absorbing compounds is about 2% or more, such as about 10% or more, such as about 15% or more, such about 25% or more of the composition.

The concentration of UV-absorbing light-scattering particles, if present, may be about 1% or more, such as from about 1% to about 10%, such as from about 2% to about 5%. In certain embodiments where the UV-sunscreen agent further includes a UV-absorbing sunscreen agent in amounts as discussed above, compositions of the present invention may have an SPF of about 20 or greater.

The compositions of the present invention may be used for a variety of cosmetic uses, especially for protection of the skin from UV radiation. The compositions, thus, may be made into a wide variety of delivery forms. These forms include, but are not limited to, suspensions, dispersions, solutions, or coatings on water soluble or water-insoluble substrates (e.g., substrates such as organic or inorganic powders, fibers, or films). Suitable product forms include lotions, creams, gels, sticks, sprays, ointments, mousses, and compacts/powders. The composition may be employed for various end-uses, such as recreation or daily-use sunscreens, moisturizers, cosmetics/make-up, cleansers/toners, anti-aging products, or combinations thereof. The compositions of the present invention may be prepared using methodology that is well known by an artisan of ordinary skill in the field of cosmetics formulation.

In order for UV-screening agents to be effective in sun screen compositions, the sun screening agents must be dissolved in at least a portion of the sun screen composition. Compositions of the present invention include a continuous water phase in which a discontinuous oil phase that includes the linear UV-absorbing polyether and additional UV-screening compounds homogeneously distributed. In certain embodiments, the linear UV-absorbing polyether and additional UV-screening compounds are dissolved, as opposed to being dispersed or suspended, within the oil phase. The oil phase may, in turn, be stabilized within the water phase. The oil phase may be such that it is present in discrete droplets or units having an average diameter of about one micron to about 1000 microns, such as from about 1 micron to about 100 microns.

The relative concentrations of water phase and oil phase may be varied. In certain embodiments the percentage by weight of water phase is from about 10% to about 90%, such as from about 40% to about 80%, such as from 50% to about 80%; wherein the balance is oil phase.

The percentage of water included in the compositions may range from about 20% to about 90%, such as from about 20% to about 80%, such as from about 30% to about 70%, such as from about 51% to about 80%, such as from about 51% to about 70%, such as from about 51% to about 60%.

Topical Carrier

The one or more linear UV-absorbing polyether and additional UV-screening compounds in the composition may be combined with a "cosmetically-acceptable topical carrier," i.e., a carrier for topical use that is capable of having the other ingredients dispersed or dissolved therein, and possessing acceptable properties rendering it safe to use topically. As such, the composition may further include any of various functional ingredients known in the field of cosmetic chemistry, for example, emollients (including oils and waxes) as well as other ingredients commonly used in personal care compositions, such as humectants, thickeners, opacifiers, fragrances, dyes, solvents for the linear UV-absorbing polyether, among other functional ingredients. Suitable examples of solvents for the UV-absorbing polyether include dicaprylyl carbonate available as CETIOL CC from Cognis Corporation of Ambler, Pennsylvania In order to provide pleasant aesthetics, in certain embodiments of the invention, the composition is substantially free of volatile solvents, and, in particular, $C_1$-$C_4$ alcohols such as ethanol and isopropanol.

Furthermore, the composition may be essentially free of ingredients that would render the composition unsuitable for topical use. As such, the composition may be essentially free of solvents such as volatile solvents, and, in particular, free of volatile organic solvents such as ketones, xylene, toluene, and the like.

Emulsifiers

The inventors surprisingly have found that UV-protective, mild sunscreens can be made by forming an oil-in-water (O/W) emulsion comprising a polymer composition comprising a linear UV-absorbing polyether and particular emulsifiers in a particular weight range. As such, compositions of the present invention include an O/W emulsifier component that includes one or more O/W emulsifiers. By "O/W emulsifier," it is meant any of a variety of molecules that are suitable for emulsifying discrete oil-phase droplets in a continuous water phase. By "low molecular weight emulsifiers," it is meant emulsifiers having a molecular weight of about 2000 daltons or less, such as about 1000 daltons or less. The O/W emulsifier may be capable of lowering the surface tension of pure deionized water to 45 dynes per centimeter when added to pure deionized water at a concentration of O/W emulsifier of 0.5% or less at room temperature. O/W emulsifiers are sometimes characterized as having a hydrophile-lipophile balance (HLB) that is about 8 or more, such as about 10 or more.

The O/W emulsifier component comprises one or more anionic emulsifiers, such that the total concentration of anionic emulsifier in the composition is about 3% or less. Examples of suitable chemical classes of anionic emulsifiers are alkyl, aryl or alkylaryl, or acyl-modified versions of the following moieties: sulfates, ether sulfates, monoglyceryl ether sulfates, sulfonates, sulfosuccinates, ether sulfosuccinates, sulfosuccinamates, amidosulfosuccinates, carboxylates, amidoethercarboxylates, succinates, sarcosinates, amino acids, taurates, sulfoacetates, and phosphates. Notable anionic emulsifiers are phosphate esters, such as cetyl phosphate salts, such as potassium cetyl phosphate. In certain embodiments, the concentration of the one or more anionic emulsifiers is from about 0.5% to about 3%, such as from about 0.6% to about 3%, such as from about 0.6% to about 2.5% of the weight of the composition. According to certain embodiments, the O/W emulsifier component consists essentially of the one or more anionic emulsifiers.

According to certain embodiments, the O/W emulsifier component is essentially free of non-ionic emulsifiers having an alcohol-functional group with a hydrocarbon chain length of 14-22 carbon atoms. Chemical classes of non-ionic emulsifiers having an alcohol functional group may include fatty alcohols, such as various saturated or unsaturated, linear or branched, $C_7$-$C_{22}$ unethoxylated, aliphatic alcohols, such as those having a single —OH group. The fatty alcohol may be derived from plant or animal oils and fats having at least one pendant hydrocarbon-comprising chain. The fatty alcohol may have from 14 to about 22 carbon atoms, such as from about 16 to about 18 carbon atoms. Examples of unbranched fatty alcohols include cetyl alcohol and stearyl alcohol.

According to certain other embodiments, the O/W emulsifier component is essentially free of cationic emulsifiers, such as alkyl quaternaries, benzyl quatemaries, ester quaternaries, ethoxylated quatemaries, and alkyl amines.

According to certain embodiments, in addition to the anonic oil-in-water emulsifier(s) discussed above, the O/W emulsifier component includes an additional emulsifier such as a non-ionic emulsifier that is devoid of alcohol functional groups, an amphoteric emulsifier, and/or a polymeric emulsifier. Examples of suitable chemical classes of non-ionic emulsifier include ethoxylates of amides; polyoxyethylene derivatives of polyol esters; noncrosslinked silicone copolymers such as alkoxy or alkyl dimethicone copolyols, silicones having pendant hydrophilic moieties such as linear silicones having pendant polyether groups or polyglycerin groups; and crosslinked elastomeric solid organopolysiloxanes comprising at least one hydrophilic moiety.

Examples of suitable chemical classes of amphoteric emulsifiers include alkyl betaines, amidoalkyl betaines, alkylamphoacetates; amidoalkyl sultaines; amphophosphates; phosphorylated imidazolines; carboxyalkyl alkyl polyamines; alkylimino-dipropionates; alkylamphoglycinates (mono or di); alkylamphoproprionates; N-alkyl β-aminoprionic acids; and alkylpolyamino carboxylates. Examples of suitable chemical classes of polymeric emulsifier include copolymers based on acrylamidoalkyl sulfonic acid such as Aristoflex® AVC and Aristoflex® HMB by Clariant Corporation; and Granthix APP by Grant Industries, Inc.

Film-Forming Polymers

Sunscreen compositions are typically formulated for enhanced water resistance with film formers. In certain embodiments of the invention, compositions of the present invention include a film forming polymer. By "film-forming polymer," it is meant a polymer that when dissolved, emulsified, or dispersed in one or more diluents, permits a continuous or semi-continuous film to be formed when it is spread with a liquid vehicle onto smooth glass, and the liquid vehicle is allowed to evaporate. As such, the polymer should dry on the glass in a manner in which over the area which it is spread should be predominantly continuous, rather than forming a plurality of discrete, island-like structures. Generally, the films formed by applying compositions on the skin according to embodiments of the invention described herein, are less than, on average, about 100 microns in thickness, such as less than about 50 microns.

In contrast to polymeric UV-absorbing polymers, film-forming polymers generally do not absorb ultraviolet radiation and therefore do not meet the requirements for UV-absorbing polymers. Film-forming polymers may be useful in compositions of the present invention in that they may enhance the UV-protection (UV-A, UV-B or both) of the composition and/or enhance the waterproofing or water resistance of the composition.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, hydrogenated dimer dilinoleyl/dimethylcarbonate copolymer, available from Cognis Corporation of Ambler, Pennsylvania as COSMEDIA DC; copolymer of vinylpyrrolidone and a long-chain a-olefin, such as those commercially available from ISP Specialty Chemicals of Wayne, New Jersey as GANEX V220; vinylpyrrolidone/tricontanyl copolymers available as GANEX WP660 also from ISP; water-dispersible polyesters, including sulfopolyesters such those commercially available from Eastman Chemical as EASTMAN AQ 38S. The amount of film-forming polymer present in the composition may be from about 0.1% to about 5%, or from about 0.10% to about 3%, or from about 0.1% to about 2%.

In certain embodiments, the composition includes an emollient used for the prevention or relief of dryness and for the protection of the skin, as well as solubilizing the linear UV-absorbing polyether. Suitable emollients include mineral oils, petrolatum, vegetable oils (e.g. triglycerides such as caprylic/capric triglyceride), waxes and other mixtures of fatty esters, including but not limited to esters of glycerol (e.g, isopropyl palmitate, isopropyl myristate), and silicone oils such as dimethicone. In certain embodiments, mixtures of triglycerides (e.g. caprylic/capric triclycerides) and esters of glycols (e.g. isopropyl myristate) may be used to solubilize the linear UV-absorbing polyethers.

In certain embodiments, the composition includes a pigment suitable for providing color or hiding power. The pigment may be one suitable for use in a color cosmetic product, including compositions for application to the hair, nails and/or skin, especially the face. Color cosmetic compositions include, but are not limited to, foundations, concealers, primers, blush, mascara, eyeshadow, eyeliner, lipstick, nail polish and tinted moisturizers.

The pigment suitable for providing color or hiding power may be composed of iron oxides, including red and yellow iron oxides, titanium dioxide, ultramarine and chromium or chromium hydroxide colors, and mixtures thereof. The pigment may be a lake pigment, e.g., an organic dye such as azo, indigoid, triphenylmethane, anthraquinone, and xanthine dyes that are designated as D&C and FD&C blues, browns, greens, oranges, reds, yellows, etc., precipitated onto inert binders such as insoluble salts. Examples of lake pigments include Red #6, Red #7, Yellow #5 and Blue #1. The pigment may be an interference pigment. Examples of interference pigments include those containing mica substrates, bismuth oxychloride substrates, and silica substrates, for instance mica/bismuth oxychloride/iron oxide pigments commercially available as CHROMALITE pigments (BASF), titanium dioxide and/or iron oxides coated onto mica such as commercially available FLAMENCO pigments (BASF), mica/titanium dioxide/iron oxide pigments including commercially available KTZ pigments (Kobo products), CELLINI pearl pigments (BASF), and borosilicate-containing pigments such as REFLECKS pigments (BASF).

The compositions of the present invention may further comprise one or more other cosmetically active agent(s). A "cosmetically active agent" is a compound that has a cosmetic or therapeutic effect on the skin, e.g., agents to treat wrinkles, acne, or to lighten the skin. The cosmetically active agent will typically be present in the composition of the invention in an amount of from about 0.001% to about 20% by weight of the composition, e.g., about 0.01% to about 10% such as about 0.1% to about 5% by weight of the composition.

In certain embodiments the composition has a pH that is from about 4.0 to about 8.0, such as from about 5.5 to about 7.0.

Sun protection factor (SPF) may be tested using the following IN-VITRO SPF TEST METHOD. The baseline transmission of a PMMA plate (substrate) without application of any test materials applied thereto was measured. Test samples were prepared by providing a sample of polymer. Blends may also be tested by this method. The polymer(s) can be tested without any additional additives; with a solvent system, or as a part of a personal care composition that may include solvent and/or additional ingredients.

Each sample is separately applied to a PMMA plate (available from Helioscience, Marseille, France) using an application density of about 32 milligrams for a 25 cm$^2$ substrate, rubbing into a uniform thin layer with the operator's finger, and allowing to dry. The samples are allowed to dry for 15 minutes before measurement of absorbance using calibrated Labsphere® UV-1000S UV transmission analyzer or a Labsphere® UV-2000S UV transmission analyzer (Labsphere, North Sutton, N.H., USA). The absorbance measures were used to calculate SPF and PFA indices (biological protection factor in the UVA based).

SPF and PFA may be calculated using methods known in the art—see equation (1) below for calculation of SPF:

$$SPF_{invitro} = \frac{\int_{\lambda=290nm}^{\lambda=400nm} E(\lambda) * I(\lambda) * d\lambda}{\int_{\lambda=290nm}^{\lambda=400nm} E(\lambda) * I(\lambda) * 10^{-A,(\lambda)} * d\lambda} \quad (1)$$

where:
$E(\lambda)$=Erythema action spectrum
$I(\lambda)$=Spectral irradiance received from the UV source A0(λ)=Mean monochromatic absorbance of the test product layer before UV exposure dλ=Wavelength step (1 nm).

Compositions of the present invention have low irritation tendencies. Irritation may be measured using, for example, the MODIFIED TEP TEST as set forth below. A lower MODIFIED TEP value of a composition tends to indicate less irritation associated therewith, as compared to a composition having a higher MODIFIED TEP value, which composition tends to cause higher levels of irritation.

Applicants have recognized that compositions of the present invention have surprisingly low MODIFIED TEP values/lower irritation associated therewith. For example, in certain embodiments, the compositions have a MODIFIED TEP value, as determined according to the MODIFIED TEP TEST as set forth below, of 0.3 or less, or about 0.25 or less, or about 0.20 or less.

The compositions of the present invention may be prepared using mixing and blending methodology that is well known by an artisan of ordinary skill. In one embodiment of the invention, a method of making a composition of the present invention includes preparing an oil phase by mixing at least the linear UV-absorbing polyether and additional UV absorbing compounds with optional oil-soluble or oil-miscible ingredients; and preparing a water phase, by mixing water and optional water-soluble or water-miscible ingredients. The oil phase and the water phase may then be mixed in a manner sufficient to homogeneously disperse the oil phase in the water phase such that the water phase is continuous and the oil phase discontinuous.

The compositions of the present invention can be used by topically administering to a mammal, e.g., by the direct laying on, wiping or spreading of the composition on the skin or hair of a human.

The following MODIFIED TEP TEST is used in the instant methods and in the following Examples. In particular, as described above, the MODIFIED TEP TEST is used to determine when a composition has reduced irritation according to the present invention.

Modified TEP Test:

The MODIFIED TEP TEST is designed to evaluate the ability of a test material to disrupt the permeability barrier formed by a confluent monolayer of Madin-Darby canine kidney (MDCK) cells. MDCK cells grown to confluence on porous filters are used to assess trans-epithelial permeability, as determined by the leakage of fluorescein dye through the monolayer. The MDCK permeability barrier is a model for the outermost layers of the corneal epithelium and this system can therefore be considered to reflect early changes in the development of eye irritation in vivo.

The following equipment is suitable for the MODIFIED TEP TEST: Packard Multiprobe 104 Liquid handling system; BioTek Washer, model number ELx405; and BioTek Powerwave XS microplate reader with a 490 nm filter. Disposable lab ware includes: Corning Support Transwell 24-well cell culture plate with microporous membrane, Cat. No. 29445-100 or 29444-580, MFG. No. 3397; Corning Receiver 24-well Tissue Culture Plate, Cat No. 29444-100, MFG. No. 3527; disposable 200 µL tips Cat. No. 82003-196; Eppendorf 5 mL combitips plus Cat No. 21516-152; Sodium Chloride 0.9% (w/v) Aqueous Cat. No. RC72105; and sterile 15 mL polypropylene centrifuge tubes. Reagents supplied by Life Technologies include: Hank's Balanced Salt Solution (10×) without Phenol Red Cat. No. 14065056 and Sodium Bicarbonate Solution, 7.5% Cat No. 25080094, Minimum Essential Medium (MEM) (1×), Cat No. 11095072, Fetal Bovine Serum, HI Cat No. 10082147, Antibiotic Antimycotic 100× Cat No. 15240096, L-Glutamine 200 mM (100×) Cat No. 25030081, Sodium Fluorescein, Sigma Cat. No. F-6377 is provided by Sigma/Aldrich.

A cell line, ATCC CCL 34 MDCK (NBL-2) (Kidney: *Canis familiaris*), is maintained in accordance ATCC (Manassas, Virginia) recommendations. Cell cultures are harvested by trypsinization and seeded into Support Transwell24 plates containing complete MEM, 48 hours prior to testing at a concentration of $5 \times 10^5$ cells per mL. Reagents are prepared: (1) 1×HBSS Buffer by combining 200 mL Hank's Balanced Salt Solution (HBSS) (10×) without phenol red with 9.3 mL Sodium Bicarbonate and increasing the volume to 2000 mL with distilled water. The pH should be in the range of 6.8-7.2 and the solution should be warmed to 37 C; (2) a 200 ug/mL stock solution of sodium fluorescein in HBSS Buffer; (3) Complete Minimum Essential Medium (MEM) is prepared by combining 100 mL's of Fetal Bovine Serum, 10 mL's of Antibiotic Antimycotic 100×, and 10 mL's of L-Glutamine 200 mM (100×) to 1000 mL's of MEM (1×).

Permeability of the membrane is confirmed by including a No Cell Control that is run with each day of testing. Sunscreen test compositions are evaluated full strength.

Inserts are washed to remove cell medium. A 24-well cell culture plate, Corning Cat No. 29445-100, containing a confluent monolayer of MDCK cells is removed from the incubator. Each 24-well cell culture plate includes an insert which holds an inner well with a microporous membrane cell growth surface suspended into a lower well. The insert containing the cell cultures is washed 5× (BioTek Washer) with warm HBSS to remove culture medium and serum. The bottom portion of the 24-well cell culture plate is washed with warm HBSS 3× and on the last wash 1 mL of HBSS is dispensed in each bottom well.

Four wells in the 24-well plate are used per sunscreen test composition, so a single 24-well plate can be used to test up to 6 sunscreen test compositions. The sunscreen test compositions are added directly to the insert well, Neat (100%), 200 µL per insert well. The 24-well cell culture plate is then returned to the incubator for a 1 hour incubation period.

Upon completion of the first incubation step, the 24-well cell culture plate is removed from the incubator and washed manually to remove test composition. Approximately 200 µL of HBSS is added to each inner well and allowed to soak for approximately 1 minute. The test composition and HBSS are then decanted from the individual wells. Any residual sample is removed by delicately flooding the inserts with HBSS and decanting. When the insert is free of residual test composition, a 10× wash (Bio Tek Washer) with warm HBSS should be done. The bottom wells are washed with warm HBSS 3× and on the last wash 1 mL of HBSS (receiver buffer) is dispensed into each bottom well.

The insert is placed back into the bottom plate containing 1 mL HBSS (receiver buffer), sodium fluorescein is added to each inner well, 200 µL per well, and the plate is returned to the incubator for a period of 45 minutes.

After the 45 minute incubation, the sodium fluorescein containing first plate is removed from the incubator, the upper insert is removed, and the amount of dye that has leaked into the receiver buffer in the lower well is determined by the Powerwave XS microplate reader. The fluorescence is read spectrophotometrically at 490 nm. Data are printed and recorded.

The insert is then placed into an empty, temporary, 24 well bottom plate on the Bio Tek Washer for a 10×HBSS wash.

Care is taken to ensure that the sodium fluorescein has been washed off and there is no residual fluorescein in the top (inner) or bottom wells.

The washed insert is placed into a fresh 24-well receiver cell culture plate, Corning Cat No. 29445-100. Both the inner wells of the insert and the bottom plate receive complete minimum essential medium (MEM), Life Technologies, Cat No. 11095072. Approximately 1 mL of complete MEM is added to the bottom wells and 200 μL is added to the inner wells. The 24-well cell culture plate is then incubated for 3 hours.

After the 3 hour incubation the 24-well cell culture plate is removed from the incubator. The insert containing the cell cultures is washed 5× (BioTek Washer) with warm HBSS to remove culture medium and serum. The bottom plate is washed with warm HBSS 3× and on the last wash 1 mL of HBSS is dispensed in each bottom well (receiver buffer).

Sodium fluorescein is added to each inner insert well, 200 μL per well, and the plate is reassembled and returned to the incubator for a period of 45 minutes.

After the 45 minute incubation, the sodium fluorescein containing plate is removed from the incubator, the insert is removed and discarded, and the amount of dye that has leaked into the lower well is determined by the Powerwave XS microplate reader. The fluorescence is read spectrophotometrically at 490 nm. Data is printed and recorded.

The spectrophotometric measurement (fluorescein leakage) value for each of the four repeats of a given sunscreen test composition is used to calculate an average fluorescein leakage value for the sunscreen test composition. The average fluorescein leakage value of the four "no cell control" wells is also calculated. The Modified TEP Score is calculated by dividing the average fluorescein leakage value of the sunscreen test composition by that of the no cell control.

Additional details of the TEP test are described in the following publication: Tchao, R. (1988) Trans-epithelial Permeability of Fluoresce in In Vitro as an Assay to Determine Eye Irritants. Alternative Methods in Toxicology 6, Progress in In Vitro Toxicology (ed. A. M. Goldberg), 271.

The values for SPF (in silico) and UVA-PF (in silico) given in the following examples are calculated according to the method described in Pure Appl. Chem. 87 (2015), 937-951.

The following examples are illustrative of the principles and practice of this invention, although not limited thereto. Numerous additional embodiments within the scope and spirit of the invention will become apparent to those skilled in the art once having the benefit of this disclosure.

EXAMPLES

Examples 1-11: Synthesis and SPF Testing of Polymer Compositions Comprising Linear UV-Absorbing Polyethers Example 1. Synthesis of a Protected Form of Glycidol

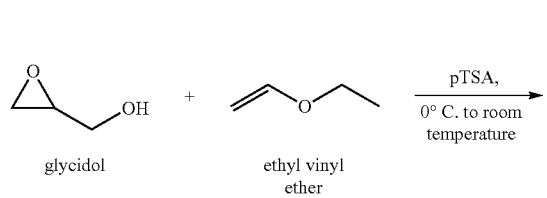

glycidol    ethyl vinyl ether

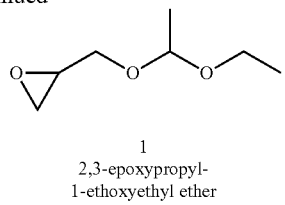

1
2,3-epoxypropyl-
1-ethoxyethyl ether

Formula VIII. Synthesis of Protected Epoxide Monomer

The synthesis of protected epoxide monomer 1 was performed as illustrated in FORMULA VIII using a variation of a procedure described in the literature (Fitton, A. et. al. *Synthesis* 1987, 1987, 1140-1142). Glycidol (53 mL, 0.80 moles) and ethyl vinyl ether (230 mL, 2.40 moles; distilled immediately before reaction) were added to a 2-neck 500 mL round bottom flask containing a magnetic stir bar. The flask was fitted with a septum and thermometer adapter; a thermometer was inserted into the adapter and positioned such that the bulb was immersed in the liquid. The flask was immersed in a brine/ice bath; the mixture was magnetically stirred. When the internal temperature was 0° C., p-toluene sulfonic acid hydrate (pTSA.H$_2$O, 1.43 g, 7.5 mmol) was added in small portions while stirring vigorously. On addition of each portion of pTSA, the temperature of the solution increased sharply; the rate of addition was slow enough to prevent the solution temperature increasing above 20° C. The final portion of pTSA was added ~5 hours after addition of the initial portion, and resulted in no exotherm; thin layer chromatography of the reaction mixture revealed no residual glycidol following the final pTSA addition. The reaction mixture was transferred into a separatory funnel; saturated aqueous NaHCO$_3$ (230 mL) was poured into the funnel slowly. The mixture was shaken, the layers allowed to separate, and the organic layer was removed, dried over sodium sulfate, and filtered through paper. The solution was concentrated by rotary evaporation, then vacuum distilled (60° C. distillate at 8 torr) affording protected epoxide monomer 1 (79.38 g) as a clear oil. NMR analysis was performed on a Varian Unity Inova 400 MHz spectrometer ($^1$H) spectrometer at 30° C.; chemical shifts are reported in parts per million (ppm) on the δ scale, and were referenced to residual protonated solvent peaks or tetramethylsilane. Spectra obtained in DMSO-d$_6$ were referenced to (CHD$_2$)(CD$_3$)SO at δ$_H$ 2.50. $^1$H NMR (400 MHz, CDCl$_3$) δ ppm 4.76 (quin, J=5.2 Hz, 1H), 3.81 (dd, J=11.5, 3.3 Hz, 1H), 3.60-3.74 (m, 3H), 3.38-3.60 (m, 4H), 3.10-3.20 (m, 2H), 2.81 (ddd, J=5.1, 4.0, 1.3 Hz, 2H), 2.63 (ddd, J=14.6, 5.1, 2.7 Hz, 2H), 1.33 (dd, J=6.2, 5.4 Hz, 6H), 1.21 (td, J=7.1, 1.3 Hz, 6H).

Example 2A. Synthesis of Linear Polyglycerol

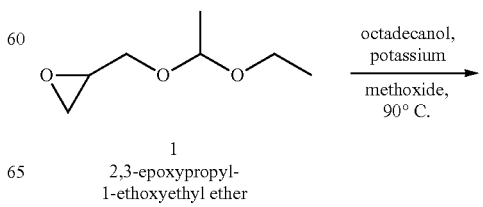

1
2,3-epoxypropyl-
1-ethoxyethyl ether

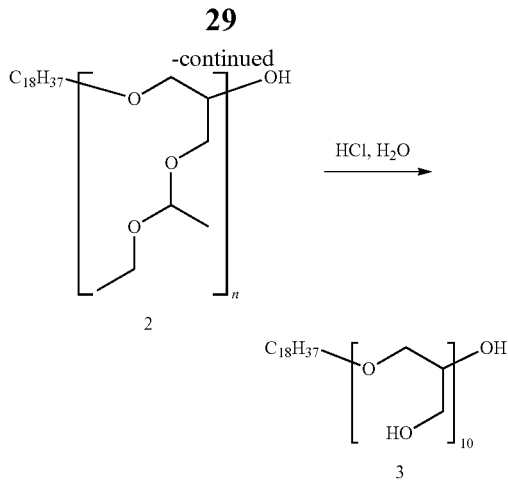

Formula IX. Synthesis of Linear Polyether Polymer

Polymerization of protected epoxide monomer 1 was achieved as illustrated in FORMULA IX. 1-Octadecanol (27.76 g, 102.6 mmol) was added to an oven-dried 250 mL 2-neck round bottom flask containing a magnetic stir bar. The flask was fitted with a nitrogen inlet adapter and rubber septum. Potassium methoxide (25 wt % in methanol (MeOH), 6.06 mL, 20.52 mmol) was added to the flask by syringe through the septum. The round bottom flask was immersed in an oil bath which had been pre-heated to 90° C. The septum was pierced with an 18 gauge needle, and the material in the flask was stirred under a constant stream of nitrogen gas for 1 hour, during which time the alcohol melted, and methanol evaporated from the flask. The septum was replaced with a pressure equalizing addition funnel containing monomer 1 (151 g, 1.04 moles). The funnel was sealed with a rubber septum. The monomer 1 was added dropwise to the stirred mixture; the reaction mixture was stirred at 90° C. for 15 hours. On cooling, this afforded crude polyether 2 as a pale brown, slightly viscous oil that was used in subsequent reactions without further purification. $^1$H NMR (400 MHz, CHLOROFORM-d) δ ppm 4.48-4.80 (m, 10H), 3.25-3.97 (m, 70H), 1.41-1.64 (m, 2H), 1.23-1.40 (m, 60H), 1.09-1.23 (m, 30H), 0.88 (t, J=7.0 Hz, 3H).

Gel permeation chromatography for molecular weight determination was performed at 35° C. on a Waters Alliance 2695 Separations Module (Waters, Milford, MA) at a flow rate of 0.5 mL/min THF (stabilized w/0.025% BHT). The 2695 was equipped with two GPC columns in series (Waters Corp HR 0.5 and HR3) with dimensions of 7.8×300 mm with 5 μm particle size) and a Waters model 410 refractive index detector. The molecular weights of the samples were determined by comparison to polystyrene standards. Standards were prepared by weighing 1-2 mg of each polystyrene (PS) polymer into a 2 mL vial with THF solvent (2 standards per vial); samples were filtered (0.22 μm) prior to analysis. Polystyrene standards spanned a range between 70,000 to 600 Daltons, and were manufactured by three vendors (Polymer Standards Service-USA, Phenomenex and Shodex). The resultant calibration curve provided an $r^2$=0.9999. Experimental samples were dissolved in THF at a concentration of 3-5 mg/mL and filtered (0.22 μm) prior to analysis. GPC (THF) analysis for polymer 2: $M_w$ 1724.

Crude polyether 2 was transferred with tetrahydrofuran (THF, ~500 mL) into a 1 L round bottom flask containing a magnetic stir bar. Concentrated aqueous HCl (37%, 20 mL) was added to the stirred reaction mixture by glass pipette. After 16 hours, the reaction mixture was concentrated by rotary evaporation to an oil which was diluted with methanol to ~500 mL. Solid NaHCO$_3$ was added in portions to the vigorously stirred solution, causing significant bubbling. When addition of the NaHCO$_3$ did not produce further bubbling (total NaHCO$_3$ added was 107 g) the mixture was filtered through paper to remove solid NaHCO$_3$. The filtrate was concentrated by rotary evaporation affording linear polyglycerol 3 as a tan foam. $^1$H NMR (400 MHz, DMSO-d$_6$) δ ppm 4.43 (br. s., 11H), 3.20-3.70 (m, 52H), 1.38-1.55 (m, 2H), 1.23 (s, 30H), 0.85 (t, J=7.0 Hz, 3H).

Example 2B. Synthesis of Linear Polyglycerol

A different batch of protected crude polymer 2 (260 g) and methanol (ACS grade, 1.25 L) was transferred into a 2 L 2-neck round bottom flask. Dry, H$^+$ form acidic ion-exchange resin in (Dowex DR-2030 from Aldrich, 446483; 100.3 g) was added to the flask. The center neck of the flask was fitted with an adapter for mechanical stirring and a paddle; the side neck of the flask was fitted with a water cooled distillation adapter. The reaction flask was immersed in an oil bath. With vigorous mechanical stirring, the reaction mixture was heated to boiling (oil bath temperature of 85° C.). Methanol (and the methyl ether resulting from removal of the protecting groups) was distilled from the flask. After 750 mL of methanol were collected, an additional portion of methanol (750 mL) was added to the reaction mixture. Another 750 mL of methanol was allowed to distill from the flask. Decolorizing charcoal was added to the hot reaction mixture. The mixture was stirred briefly and then filtered through paper. The filtrate was concentrated by rotary evaporation. Residual solvent was removed under vacuum affording the final linear polyglycerol as a yellowish foam (107 g).

Example 3A. Synthesis of Benzotriazole Chromophore Carboxylate

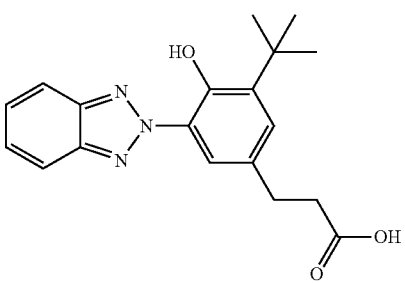

Formula X. Benzotriazole Carboxylate

The polyethylene glycol ester of 3-[3-(2H-1,2,3-benzotriazol-2-yl)-5-tert-butyl-4-hydroxyphenyl]propanoate (a chromophore sold under the trade name TINUVIN 213 by BASF Corporation, Wyandotte, Michigan) (81.0 g) was added to a 2 L round bottom flask containing a magnetic stir bar. EtOH (600 mL) was added to the flask by funnel, and the mixture was stirred until homogeneous. Sodium hydroxide (NaOH, 30.8 g) was dissolved in H$_2$O (400 mL); the basic solution was transferred into an addition funnel above the 2 L flask. The NaOH solution was added slowly to the stirred mixture; the pale amber cloudy solution immediately turned clear and dark orange. When addition was complete, the mixture was stirred overnight at room temperature. The solution was concentrated by rotary evaporation to remove most of the EtOH. The resulting orange oil was diluted to 1400 mL with $H_2O$. The mixture was stirred mechanically and was acidified to ~pH 1 by addition of 1 M aq. HCl (~700 mL). The resulting white precipitate was filtered and pressed to remove water, then recrystallized from EtOH. The first crop of crystals were long, thin colorless needles. The supernatant was removed and concentrated by rotary evaporation; a second crop of material was isolated as a white, amorphous solid. The two crops were combined and dried in a vacuum oven overnight affording a UV-chromophore having a carboxylate group, specifically benzotriazole carboxylate 4, 3-(3-(2H-benzo[d][1,2,3]triazol-2-yl)-5-(tert-butyl)-4-hydroxyphenyl) propanoic acid (37.2 g) as a white solid; the structure is illustrated in FORMULA X. $^1$H NMR (400 MHz, DMSO-$d_6$) δ ppm 11.25 (br. s, 1H), 8.00-8.20 (m, 2H), 7.95 (d, J 2.1 Hz, 1H), 7.50-7.67 (m, 2H), 7.28 (d, J 2.1 Hz, 1H), 2.87 (t, J 7.5 Hz, 2H), 2.56 (t, J 7.5 Hz, 2H), 1.45 (s, 9H).

Example 3B. Synthesis of Benzotriazole Chromophore Carboxylate

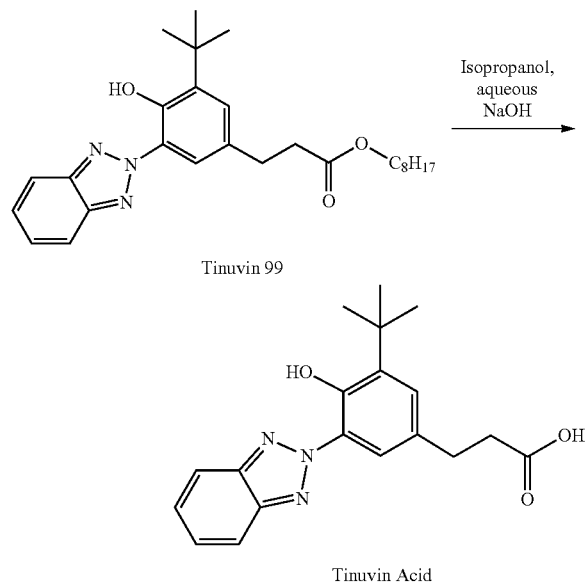

Benzenepropanoic acid, 3-(2H-benzotriazol-2-yl)-5-(1,1-dimethylethyl)-4-hydroxy-, C7-9-branched and linear alkyl esters, commercially available as TINUVIN 99 from BASF (120 g, 265.7 mmol) was added to a 3 L single neck round bottom flask containing a magnetic stir bar. Isopropanol (900 ml, ACS grade) was added to the flask, and the resulting mixture was stirred until complete dissolution. Sodium hydroxide (36 g, 900 mmol) was dissolved in 600 ml of distilled water, and the solution was added to the reaction mixture. The resulting opaque mixture, which in 40 min became a clear orange solution, was stirred at room temperature for 24 hours, and then slowly added to a vigorously stirred mixture of isopropanol (1800 ml, ACS grade) and 1N HCl (1200 ml), cooled to 10-15° C. The precipitated white solid was filtered, washed with 1.2 L of 1:1 isopropanol-1N HCl mixture, suspended in 2 L of 0.25N HCl, stirred for 1 hour, filtered and dried at 90° C. in a vacuum oven overnight. The resulting UV-chromophore having a carboxylate group, specifically a benzotriazole carboxylate 4 (37.2 g) was obtained as a pale yellow solid, 85 g, 94.5%.

Example 4A. Esterification of Polyether Backbone with Benzotriazole Carboxylate

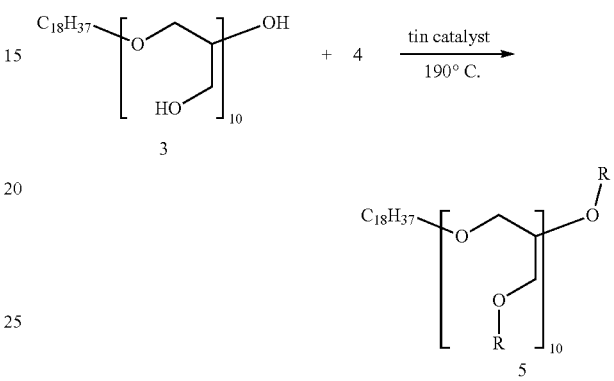

Formula XI. Esterification of Polyglycerol with Benzotriazole Carboxylate

FORMULA XI illustrates the esterification of polyglycerol 3 with benzotriazole carboxylate 4 using catalytic tin. Linear polyglycerol 3 of Example 2A (5.52 g, 60.1 hydroxyl milliequivalents) was dissolved in methanol and transferred into a 500 mL 2-neck round bottom flask. The methanol was removed using rotary evaporation; benzotriazole carboxylate 4 (20.38 g, 60.1 mmol)) and a magnetic stir bar were added to the flask. The flask was fitted with a nitrogen inlet adapter and vacuum distillation adapter with 100 mL receiving flask. The flask was placed under vacuum (<1 Torr) for 1 hour, then backfilled with nitrogen gas. The inlet adapter was removed from the 500 mL flask; tin (II) ethyl hexanoate (49 μL, 0.15 mmol) was added to the flask by syringe under a stream of nitrogen. The apparatus was reassembled and immersed in an oil bath pre-heated to 200° C. When most of the solid had melted, the oil bath was cooled to 190° C. The reaction was stirred under a flow of nitrogen for 16 hours. While maintaining temperature and stirring, the reaction flask was then placed under vacuum (<1 Torr) for an additional 24 hours. The apparatus was then backfilled with nitrogen and cooled to room temperature. The material was freeze fractured and ground to powder using a mortar and pestle. The powder was dissolved in a minimal amount of THF. Methanol (900 mL) and a magnetic stir bar were added to an Erlenmeyer flask; the flask was immersed in an ice bath. The THF solution was added to the methanol with vigorous stirring; the resulting precipitate was isolated by vacuum filtration. Residual solvent was removed under vacuum overnight, affording the linear polyglycerol 5 (18.7 g) as an off-white solid. $^1$H NMR (400 MHz, CDCl$_3$) δ ppm 11.71 (br. s., 9H), 8.03 (br. s., 9H), 7.80 (br. s, 18H), 7.28-7.48 (m, 18H), 7.12 (br. s, 9H), 5.19 (br. s, 1H), 3.98-4.46 (br. m, 20H), 3.21-3.61 (br. m, 32H), 2.91 (br. s, 18H), 2.67 (br. s, 18H), 1.38-1.51 (m, 85H), 1.13-1.35 (m, 28H), 0.87 (t, J=6.6 Hz, 3H). GPC (THF): Mw 3299; M$_n$ 2913.

Example 4B Synthesis of Linear UV-Absorbing Polyether (Actual Process)

Example 5. Conversion of Benzotriazole Carboxylate to Acid Chloride (3-(3-(2H-benzo[d][1,2,3]triazol-2-yl)-5-(tert-butyl)-4-hydroxyphenyl)propanoyl chloride)

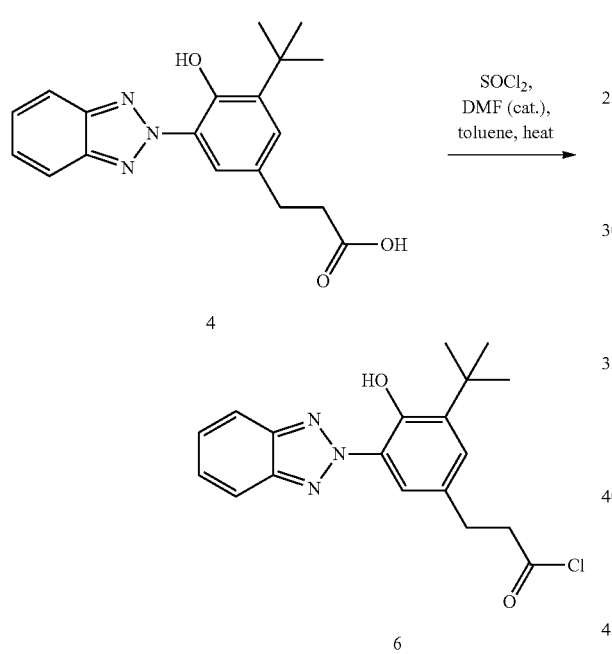

Formula XII. Conversion of Benzotriazole Carboxylate to Benzotriazole Acid Chloride The conversion of the benzotriazole carboxylic acid 4 to the corresponding benzotriazole acid chloride 6 is illustrated in FORMULA XII. Benzotriazole carboxylate 4 (50 g 147 mmol, synthesized as described in Example 3 was added to a 1000 mL 3-neck flask containing a magnetic stir bar; the flask was equipped with a reflux condenser, nitrogen inlet, and rubber septum. Anhydrous toluene (~500 mL) was transferred into the flask by cannula through the septum. Thionyl chloride (16.1 mL, 221 mmol) was transferred into the flask by syringe; dimethylformamide (2.7 mL) was then added to the flask by syringe. The flask was immersed in an oil bath set at 80° C.; the suspension was stirred; the solids began to disperse, eventually yielding a clear solution. After ~4 hours, the reaction mixture was allowed to cool, transferred to a round bottom flask and concentrated by rotary evaporation. The resulting oil was triturated with hexanes, affording a beige solid. The suspension of material was recrystallized by adding additional hexanes and warming to reflux, filtration through paper, and slow cooling to room temperature with stirring. The resulting beige crystals were filtered and dried under vacuum at 50° C. The filtrate was concentrated, and the recrystallization performed a second time affording a second crop of crystals; the mass of the combined crops of benzotriazole acid chloride 6 was 44.7 grams. $^1$H NMR (400 MHz, CDCl$_3$) δ 11.88 (s, 1H), 8.16 (d, J=2.2 Hz, 1H), 7.91-7.98 (m, 2H), 7.47-7.54 (m, 2H), 7.21 (d, J=2.2 Hz, 1H), 3.29 (t, J=7.5 Hz, 2H), 3.07 (t, J=7.5 Hz, 2H), 1.50-1.53 (s, 9H).

Example 6. Conversion of Benzotriazole Acid Chloride to Isocyanate (2-(2H-benzo[d][1,2,3]triazol-2-yl)-6-(tert-butyl)-4-(2-isocyanatoethyl)phenol)

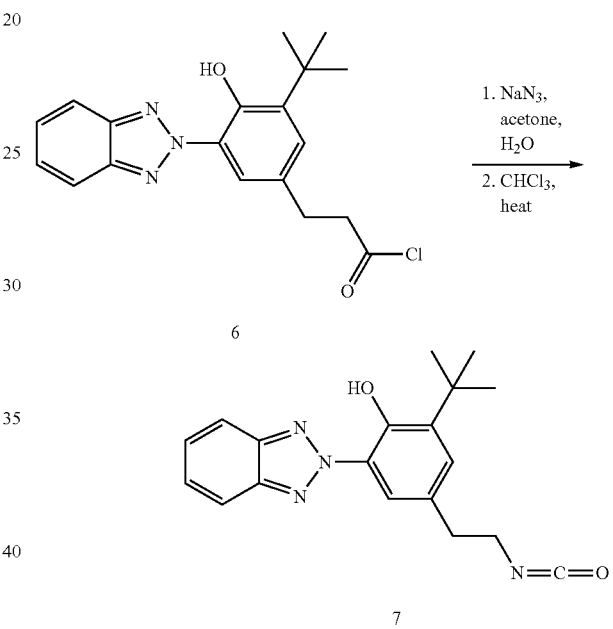

Formula XIII. Conversion of Acid Chloride to Isocyanate

Synthesis of a benzotriazole isocyanate 7 suitable for coupling to pendant functional groups is illustrated in FORMULA XIII. Sodium azide (NaN$_3$, 2.5 g, 38 mmol: CAUTION!NaN$_3$ is a violent poison) was carefully transferred into a single necked 500 mL round bottom flask containing a magnetic stir bar. Deionized water (20 mL) was added to the flask; the NaN$_3$ dissolved with mixing affording a clear solution. The flask was immersed in an ice bath. Acid chloride 6 (7.0 g 20 mmol) and anhydrous acetone (45 mL) were transferred into a pressure equalizing addition funnel in a positive pressure N$_2$ atmosphere glove box. The acid chloride dissolved in the acetone with gentle swirling, affording a clear yellow solution. The addition funnel containing benzotriazole acid chloride 6 was fitted into the flask containing the aqueous solution of NaN$_3$; the top of the addition funnel was fitted with a N$_2$ adapter connected to a vacuum gas manifold. The solution of benzotriazole acid chloride 6 was added dropwise to the NaN$_3$ solution. After addition of several drops, a white precipitate began to appear, suspended in the aqueous solution. Addition of benzotriazole acid chloride 6 was complete within 30 minutes; mixing was continued for 20 minutes in the ice bath. Water (30 mL) was added to the resulting white slurry; solids were collected by filtration through a glass fritted funnel under vacuum. The white solid was transferred to a separatory funnel followed with CHCl$_3$ (185 mL). The flask was shaken and the layers were allowed to separate. The lower organic phase was removed from the small aqueous layer and dried over Na$_2$SO$_4$. The solution was filtered; the filtrate was placed in a single necked 500 mL round bottom flask containing a magnetic stir bar; the flask was fitted with a reflux condenser with nitrogen inlet adapter and immersed in an oil bath. The solution was heated slowly to reflux over 30 minutes. The final oil bath temperature was 65° C. As the oil bath temperature surpassed 55° C., bubbling was apparent in the solution. The reaction was allowed to reflux for a total of 90 min. CHCl$_3$ was then removed by rotary evaporation; the resulting oil crystallized overnight on standing affording the benzotriazole isocyanate 7 (5.8 g) as a slightly grey solid. $^1$H NMR (400 MHz, CDCl$_3$) δ 11.91 (s, 1H), 8.18 (d, J=1.9 Hz, 1H), 7.92-7.98 (m, 2H), 7.47-7.53 (m, 2H), 7.23 (d, J=2.1 Hz, 1H), 3.59 (t, J=6.9 Hz, 2H), 2.96 (t, J=6.9 Hz, 2H), 1.52 (s, 9H).

Example 7. Coupling of Isocyanate to Polyglycerol

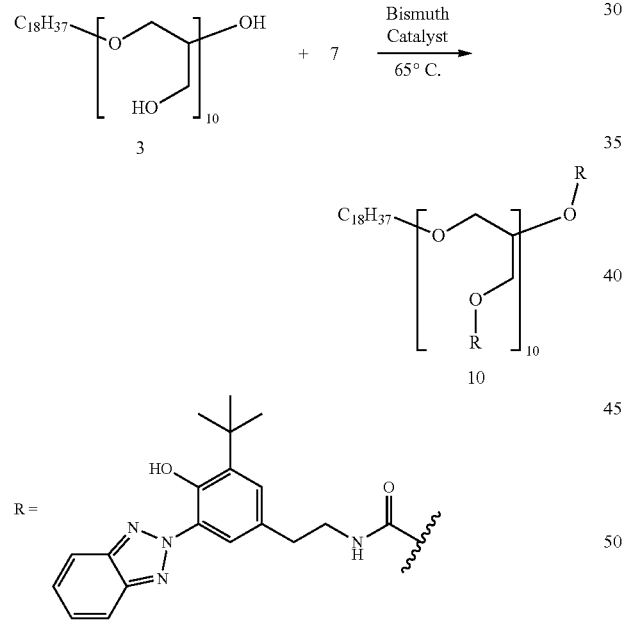

Formula XIV. Reaction of Polyglycerol with Isocyanate

The reaction of linear polyglycerol 3 with benzotriazole isocyanate 7 is illustrated in FORMULA XIV.

A solution of polyglycerol 3 in methanol was concentrated by rotary evaporation; residual solvent was removed in a vacuum oven overnight at 75° C. The polymer (2.22 g, 24.1 hydroxyl milliequivalents) was added to a 100 mL 2-neck round bottom flask containing a magnetic stir bar. Isocyanate 7 (7.65 g, 22.7 mmol), bismuth catalyst (25 mg; a bismuth carboxylate complex sold under the trade name BICAT 8210 by Shepherd Chemical, Norwood, OH) and THF (17.4 ml, dried over 3 angstrom molecular sieves) were added to the flask. The flask was placed in a 65° C. heated oil bath and fitted with a gas inlet. The reaction mixture was stirred for 5 hours under a nitrogen atmosphere, then allowed to cool to room temperature. FTIR was used to confirm the disappearance of the strong isocyanate peak at 2250 cm$^{-1}$. The reaction mixture was poured into 160 ml of methanol, resulting in a tan precipitate. Methanol was decanted off and the product was washed in the flask with methanol (2×75 mL). Residual solvent was removed in a vacuum oven overnight at 60° C.; the material was ground to a fine powder.

Example 8. Synthesis of an Epoxide Chromophore for the Direct Polymerization Method

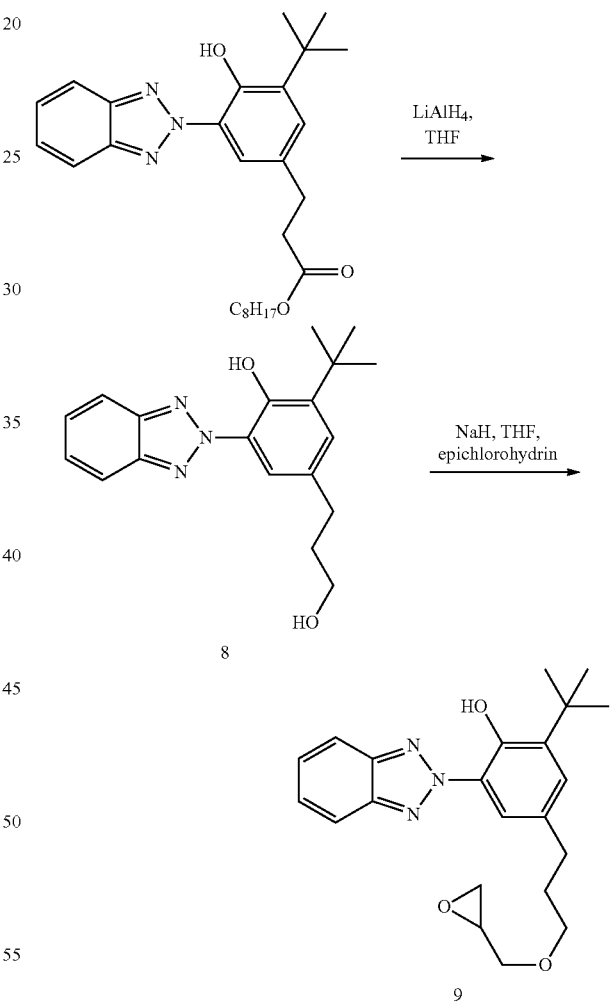

Formula XV. Synthesis of Epoxide Chromophore Monomer

The synthesis of an epoxide monomer 9 bearing a benzotriazole chromophore is illustrated in FORMULA XV. A solution of lithium aluminum hydride (LAH) in THF (a 1 M, 250 mL) was transferred by cannula under nitrogen atmosphere into an oven-dried 500 mL 2-neck round bottom flask containing a magnetic stir bar and fitted with a rubber septum and pressure equalizing addition funnel. The reaction flask was immersed in an ice bath; stirring was started. Benzenepropanoic acid, 3-(2H-benzotriazol-2-yl)-5-(1,1-dimethylethyl)-4-hydroxy,C7-C9 branched and linear alkyl ester containing 5 wt. % 1-methoxy-2-propyl acetate (50.06 g; a benzotriazole UV absorbing product sold under the trade name TINUVIN 99-2 by BASF Corporation, Wyandotte, Michigan) was transferred into the addition funnel, and dissolved in anhydrous THF (30 mL). The THF solution containing the benzotriazole was added dropwise to the solution containing LAH; this resulted in slow fizzing. After the addition was complete, an additional portion of LAH solution (100 mL) was cannulated into the reaction flask. The reaction was allowed to warm to room temperature with stirring. After 2 hours, the reaction mixture was poured into a 1 liter erlenmeyer flask which was immersed in an ice bath. The solution was stirred mechanically while water (~60 mL) was added slowly to quench any residual LAH (EXTREME CAUTION: quenching of LAH with water is exothermic and releases large quantities of highly flammable $H_2$ gas). When the LAH was quenched (no additional gas released with additional water), the grey suspension was diluted to 1 L with 1 M aqueous HCl. This solution was transferred into a 2 L separatory funnel and extracted with ethyl acetate (1×400 mL, then 2×50 mL). The combined ethyl acetate layers were washed with brine (1×400 mL), dried over $Na_2SO_4$, then filtered through paper. Solvent was removed first by rotary evaporation and then in a vacuum oven overnight affording benzotriazol alcohol 8 (42.16 g) as a beige solid with a strong unpleasant odor. $^1$H NMR (400 MHz, CDCl$_3$) δ ppm 11.75 (s, 1H), 8.15 (d, J=2.1 Hz, 1H), 7.88-7.99 (m, 2H), 7.43-7.52 (m, 2H), 7.22 (d, J=2.1 Hz, 1H), 3.75 (m, 2H), 3.62 (br. s, 1H), 2.77 (t, J=7.7 Hz, 2H), 1.91-2.06 (m, 2H), 1.52 (s, 9H).

Sodium hydride (6.0 g, 250 mmol) was added to an oven-dried 3-neck round bottom flask containing a magnetic stirring bar. The flask was fitted with a pressure equalizing addition funnel, nitrogen inlet adapter and rubber septum. Anhydrous THF (300 mL) was added to the flask by cannula under nitrogen; the flask was then immersed in an ice bath, and stirring was starting. Benzotriazol Alcohol 8 (20.0 g, 61.5 mmol) and a small magnetic stirring bar were added to the addition funnel; THF was cannulated into the addition funnel, and the stir bar was agitated to promote dissolution of the alcohol in the THF. The final volume of the alcohol/THF solution was 65 mL. This solution was added dropwise to the cold, stirred sodium hydride suspension. The cold reaction mixture was stirred for 1 hour, then epichlorohydrin (20 mL, 256 mmol) was added by syringe through the septum. The addition funnel was exchanged with a reflux condenser with nitrogen inlet, and the round bottom flask was immersed in an oil bath at 70° C. The mixture was stirred for 19 hours, then the mixture was transferred to a separatory funnel with 1M aqueous HCl (750 mL) and ethyl acetate (500 mL). After shaking, the aqueous layer was discarded. The organic layer was washed with water (2×250 mL) and brine (1×250 mL) then dried over $Na_2SO_4$. The solution was concentrated by rotary evaporation. The crude product was purified by chromatography on silica gel (6:1 hexanes/ethyl acetate). Fractions containing the desired product were pooled, concentrated by rotary evaporation; residual solvent was removed under vacuum overnight affording the epoxide monomer 9 bearing a benzotriazole chromophore (7.35 g) as a beige solid. $^1$H NMR (400 MHz, CDCl$_3$) δ ppm 11.77 (s, 1H), 8.14 (d, J=1.9 Hz, 1H), 7.85-8.00 (m, 2H), 7.41-7.53 (m, 2H), 7.21 (d, J=1.9 Hz, 1H), 3.74 (dd, J=11.5, 3.1 Hz, 1H), 3.57 (ddt, J=19.8, 9.3, 6.4 Hz, 2H), 3.43 (dd, J=11.5, 5.8 Hz, 1H), 3.19 (ddt, J=5.8, 4.0, 2.9 Hz, 1H), 2.82 (br. t, J=4.7 Hz, 1H), 2.76 (br. t, J=7.7 Hz, 2H), 2.64 (dd, J=5.1, 2.6 Hz, 1H), 1.93-2.04 (m, 2H), 1.52 (s, 9H).

Example 9. Esterification of Alternate Polyglycerol with Benzotriazole Acid

A polyglycerol partially esterified with stearic acid (2.5 g, 19.8 hydroxy milliequivalents; tetradecaglyceryl monostearate sold under the trade name POLYALDO 14-1-S by Lonza, Allendale, NJ) and benzotriazole carboxylate 4 (8.8 g, 23.8 mmol) were transferred into a 2-neck 100 mL round bottom flask containing a magnetic stir bar. The flask was fitted with a nitrogen inlet adapter and distillation adapter with 100 mL receiving flask. The apparatus was placed under vacuum for one hour, then backfilled with nitrogen. The distillation head was removed, and tin (II) ethyl hexanoate (50 µL) was added to the reaction flask by syringe under nitrogen flow. The apparatus was reassembled, then purged under vacuum and backfilled with nitrogen 3 times. The reaction flask was immersed in an oil bath that was warmed to 180° C. with constant flow of nitrogen into the 2-neck flask through the distillation adapter and out of the vacuum adapter to room atmosphere. The reaction was stirred for three hours and then cooled to room temperature under nitrogen flow, affording the product, a UV-absorbing polyglycerol, as a yellow solid. $^1$H NMR (400 MHz, CDCl$_3$) δ ppm 11.81 (br. s., 2H), 8.15 (br. s., 2H), 7.75-8.02 (br. s, 4H), 7.34-7.58 (br. s, 4H), 7.21 (br. s., 2H), 4.93-5.32 (br, 1H), 3.17-4.50 (br. m, 38H), 2.86-3.11 (br. m, 4H), 2.54-2.84 (br. m, 4H), 2.31 (br. s., 2H), 1.61 (br. s., 2H), 1.50 (br. s., 18H), 1.26 (br. s., 28H), 0.89 (t, J=6.3 Hz, 3H). GPC (THF): $M_w$ 1700; $M_n$ 950.

Example 10. Synthesis of Benzotriazole Acid Methyl Ester

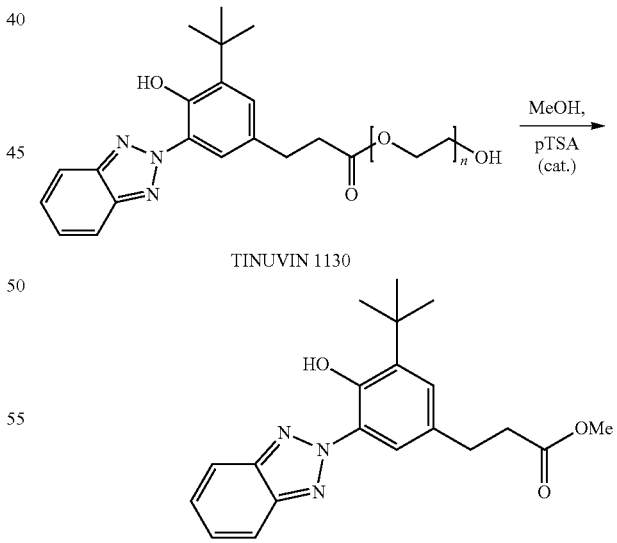

Formula XVI. Synthesis of Methyl Ester 11

The synthesis of benzotriazole methyl ester 11 intended for transesterification with a polymer with hydroxyl functional groups is illustrated in FORMULA XVI. Beta-[3-(2-H-benzotriazole-2-yl)-4-hydroxy-5-tert-butylphenyl]-propionic acid-poly(ethylene glycol) 300-ester (50.1 g; a UV absorbing product sold under the trade name TINUVIN 1130 by BASF Corporation, Wyandotte, Michigan) was added to a 2-neck 1 liter round bottom flask containing a magnetic stir bar. Methanol (500 mL) was added to the flask. The flask was immersed in an oil bath; the solution was stirred. p-TSA.H$_2$O (0.63 g) was added to the solution. The 2-neck flask was fitted with a reflux condenser and rubber septum; the stirred reaction mixture was brought to reflux by warming the oil bath; reflux was maintained for 17 hours. The flask was then removed from the oil bath and allowed to cool to room temperature, whereupon the product precipitated as a white solid. The precipitate was isolated by vacuum filtration, and then recrystallized from methanol; the solids were isolated by vacuum filtration and dried under vacuum at 80° C. affording the benzotriazole methyl ester 11 (18.27 g) as a white solid. $^1$H NMR (400 MHz, CDCl$_3$) δ ppm 11.81 (s, 1H), 8.16 (d, J=2.1 Hz, 1H), 7.90-7.98 (m, 2H), 7.45-7.53 (m, 2H), 7.22 (d, J=2.2 Hz, 1H), 3.71 (s, 3H), 3.01 (t, J=7.8 Hz, 2H), 2.71 (t, J=7.8 Hz, 2H), 1.51 (s, 9H).

Example 11. Transesterification of Benzotriazole Methyl Ester with Polyglycerol Polymer

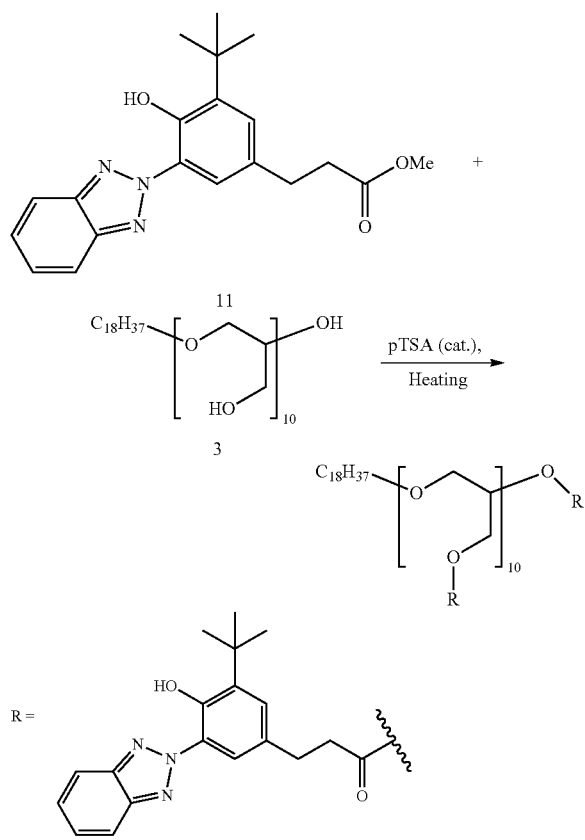

Formula XVII. Transesterification of with Polyglycerol

The transesterification of benzotriazole methyl ester 11 with polyglycerol 3 is illustrated in FORMULA XVII. A solution of polyglycerol 3 solution in MeOH was concentrated by rotary evaporation; residual solvent was removed overnight under vacuum at 75° C. Polyglycerol 3 (1.36 g, 14.9 hydroxyl milliequivalents) was added to a 100 mL 2-neck round bottom flask containing a magnetic stir bar. Benzotriazole methyl ester 11 (4.24 g, 12 mmol) and pTSA.H$_2$O (7.1 mg) was added to the flask. The flask was fitted with a nitrogen inlet adapter and distillation adapter with 100 mL receiving flask. The reaction flask was immersed in an oil bath, and the oil bath was warmed to 175° C. Within 20 minutes, all of the reactants had melted. The reaction mixture was stirred vigorously under a stream of nitrogen overnight. The following morning, the flask was placed under vacuum; residual UV-chromophore sublimed and collected in the distillation adapter. Heating under vacuum was continued overnight. The reaction mixture was then cooled to room temperature; the UV-absorbing polyglycerol product was obtained as a yellow, glassy solid. $^1$H NMR (400 MHz, CDCl$_3$) δ ppm 11.71 (br. s., 8H), 8.05 (br. s., 8H), 7.81 (br. s., 16H), 7.36 (br. s., 16H), 7.14 (br. s., 8H), 5.06-5.32 (br. s., 1H), 3.86-4.57 (m, 16H), 3.15-3.82 (m, 30H), 2.92 (br. s., 16H), 2.68 (br. s., 16H), 1.45 (br. s., 76H), 1.24 (br. s., 28H), 0.88 (t, J=6.6 Hz, 3H).

It can be seen from Examples 1-11 that analytical characterization of the resulting linear UV-absorbing polyethers was consistent with the expected structures. HPLC analysis of the polymers described in the examples provided evidence that the polymerization methods described resulted in low concentrations of residual UV absorbing monomer.

Example 12: Preparation of Sunscreen Compositions Containing a Combination of a Linear Ultraviolet Radiation-Absorbing Polyethermer and Other Ultraviolet-Screening Compounds COMPOSITION EXAMPLES 1-8 Examples 1-8 illustrate the linear UV-Absorbing Polyether can be formulated with avobenzone. The UV-Absorbing polyether was made consistent with the method described in Example 3B and Example 4A.

Examples 1-8 were prepared using a standard sunscreen emulsion containing either 3% or 1% avobenzone, 20% or 10% linear UV-Absorbing Polyether, or the combination of avobenzone and linear UV-Absorbing Polyether at indicated concentrations as shown in Tables 2 and 3 described below.

TABLE 2

| TRADE NAME | INCI | Example 1 % Wt | Example 2 % Wt | Example 3 % Wt | Example 4 % Wt |
|---|---|---|---|---|---|
| AGUA PURIFICADA | Aqua | 48.60 | 65.60 | 45.60 | 55.60 |
| Linear UV-Absorbing Polyether (14-1-S HLS) | Polyglceryl Ester + Tinuvin | 20.00 | | 20.00 | 10.00 |
| Cetiol CC | Dicaprylyl Carbonate | 20.00 | 20.00 | 20.00 | 20.00 |
| AMPHISOL K | Potassium Cetyl Phosphate | 2.00 | 2.00 | 2.00 | 2.00 |
| Antaron V220 | VP/Eicosene Copolymer | 2.00 | 2.00 | 2.00 | 2.00 |
| ANTARON WP 660 | Tricontanyl PVP | 2.00 | 2.00 | 2.00 | 2.00 |
| Silisphere 6M | Silica | 1.50 | 1.50 | 1.50 | 1.50 |
| Arlacel 165-FP-PA | Glyceryl Stearate; PEG-100 Stearate | 1.00 | 1.00 | 1.00 | 1.00 |

TABLE 2-continued

| TRADE NAME | INCI | Example 1 % Wt | Example 2 % Wt | Example 3 % Wt | Example 4 % Wt |
|---|---|---|---|---|---|
| Neo Heliopan 357 | Avobenzone | | 3.00 | 3.00 | 3.00 |
| White Beeswax SP-422P | Beeswax | 0.80 | 0.80 | 0.80 | 0.80 |
| Phenoxyethanol | Phenoxyethanol | 0.60 | 0.60 | 0.60 | 0.60 |
| Sensiva SC-50 (Schulke & Mayr) | Ethylhexyl-glycerin | 0.50 | 0.50 | 0.50 | 0.50 |
| Lexgard O | Caprylyl Glycol | 0.40 | 0.40 | 0.40 | 0.40 |
| Edeta BD | Disodium EDTA | 0.20 | 0.20 | 0.20 | 0.20 |
| Pemulen TR-1 | Acrylates/C10-30 Alkyl Acrylate Crosspolymer | 0.20 | 0.20 | 0.20 | 0.20 |
| Soda Cáustica Líquida BL | Sodium Hydroxide | 0.10 | 0.10 | 0.10 | 0.10 |
| ELESTAB CPN | Chlorphenesin | 0.10 | 0.10 | 0.10 | 0.10 |
| TOTAL | | 100.00 | 100.00 | 100.00 | 100 |

TABLE 3

| TRADE NAME | INCI | Example 5 % Wt | Example 6 % Wt | Example 7 % Wt | Example 8 % Wt |
|---|---|---|---|---|---|
| AGUA PURIFICADA | Aqua | 63.60 | 47.60 | 57.60 | 66.60 |
| Linear UV-Absorbing Polyether (14-1-S HLS) | Polyglceryl Ester + Tinuvin | 2.00 | 20.00 | 10.00 | 1.00 |
| Cetiol CC | Dicaprylyl Carbonate | 20.00 | 20.00 | 20.00 | 20.00 |
| AMPHISOL K | Potassium Cetyl Phosphate | 2.00 | 2.00 | 2.00 | 2.00 |
| Antaron V220 | VP/Eicosene Copolymer | 2.00 | 2.00 | 2.00 | 2.00 |
| ANTARON WP 660 | Tricontanyl PVP | 2.00 | 2.00 | 2.00 | 2.00 |
| Silisphere 6M | Silica | 1.50 | 1.50 | 1.50 | 1.50 |
| Arlacel 165-FP-PA | Glyceryl Stearate; PEG-100 Stearate | 1.00 | 1.00 | 1.00 | 1.00 |
| Neo Heliopan 357 | Avobenzone | 3.00 | 1.00 | 1.00 | 1.00 |
| White Beeswax SP-422P | Beeswax | 0.80 | 0.80 | 0.80 | 0.80 |
| Phenoxyethanol | Phenoxyethanol | 0.60 | 0.60 | 0.60 | 0.60 |
| Sensiva SC-50 (Schulke & Mayr) | Ethylhexyl-glycerin | 0.50 | 0.50 | 0.50 | 0.50 |
| Lexgard O | Caprylyl Glycol | 0.40 | 0.40 | 0.40 | 0.40 |
| Edeta BD | Disodium EDTA | 0.20 | 0.20 | 0.20 | 0.20 |
| Pemulen TR-1 | Acrylates/C10-30 Alkyl Acrylate Crosspolymer | 0.20 | 0.20 | 0.20 | 0.20 |
| Soda Cáustica Líquida BL | Sodium Hydroxide | 0.10 | 0.10 | 0.10 | 0.10 |
| ELESTAB CPN | Chlorphenesin | 0.10 | 0.10 | 0.10 | 0.10 |
| TOTAL | | 100.00 | 100.00 | 100.00 | 100 |

COMPOSITION EXAMPLES 9-11 Examples 9-11 illustrate the linear UV-Absorbing Polyether can be formulated with other UV absorbing compounds. The linear UV-Absorbing polyether was made consistent with the method described in Example 3B and Example 4A. Examples 9-11 were prepared using a standard sunscreen emulsion as shown in Table 4 described below, by heating phase A and B to 80° C. then adding phase A into B to homogenize then cooling to room temperature and continued stirring for a while. pH value 6.00-6.40

TABLE 4

| Trade Name | INCI-Name | Example 9 % (w/w) as supplied | Example 10 % (w/w) as supplied | Example 11 % (w/w) as supplied |
|---|---|---|---|---|
| Phase A | | | | |
| Eumulgin ® SG | Sodium Stearoyl Glutamate | 2.00 | 2.00 | 2.00 |
| Lanette ® 18 | Stearyl Alcohol | 1.00 | 1.00 | 1.00 |
| Cetiol ® B | Dibutyl Adipate | 14.00 | 14.00 | 14.00 |
| Cetiol ® AB | C12-15 Alkyl Benzoate | 5.00 | 5.00 | 5.00 |
| Finsolv EB | Ethylhexyl Benzoate | 3.00 | 3.00 | 3.00 |
| Euxyl PE9010 | Phenoxyethanol (and) Ethylhexylglycerin | 1.00 | 1.00 | 1.00 |
| Uvinul ® T150 | Ethylhexyl Triazone | 3.00 | 3.00 | 3.00 |
| Uvinul® A Plus | Diethylamino Hydroxybenzoyl Hexyl Benzoate | 10.00 | 10.00 | 10.00 |
| Tinosorb ® S | Bis-Ethylhexyloxyphenol Methoxyphenyl Triazine | 3.00 | | 1.00 |
| Linear UV-Absorbing Polyether (14-1-S HLS) | Polygiceryl Ester + Tinuvin | | 6.00 | 4.00 |
| Phase B | | | | |
| Water, demin. | Aqua | Qs. 100 | Qs. 100 | Qs. 100 |
| Glycerin | Glycerol | 3.00 | 3.00 | 3.00 |
| Cosmedia SP | Sodium Polyacrylate | 0.60 | 0.60 | 0.60 |
| Keltrol CG-RD | Xanthan Gum | 0.50 | 0.50 | 0.50 |
| EDTA BD | Disodium EDTA | 0.20 | 0.20 | 0.20 |
| SPF (in silico) | | 30.1 | 30.1 | 30.1 |
| UVA-PF (in silico) | | 26.7 | 26.5 | 26.6 |

COMPOSITION EXAMPLES 12-14 Examples 12-14 illustrate the linear UV-Absorbing Polyether can be formulated with other UV absorbing compounds. The linear UV-Absorbing polyether was made consistent with the method described in Example 3B and Example 4A. Examples 12-14 were prepared using a standard sunscreen emulsion as shown in Table 5 described below, by heating phase A to 75° C. under stirring followed by heating up phase B without Amphisol K to 75° C. under stirring. At 75° C. added Amphisol K into phase B, continue stirring. Add phase A into phase B under stirring to homogenize. Cool down to 40° C. under stirring. Add the ingredients of phase C and D under stirring. Cool down to room temperature under stirring. pH value 6.0.

TABLE 5

| Trade Name | INCI-Name | Example 12 % (w/w) as supplied | Example 13 % (w/w) as supplied | Example 14 % (w/w) as supplied |
|---|---|---|---|---|
| Phase A | | | | |
| Cetiol ® B | Dibutyl Adipate | 15.00 | 15.00 | 15.00 |
| Cetiol ® AB | C12-15 Alkyl Benzoate | 14.00 | 14.00 | 14.00 |
| Lanette ® O | Cetearyl Alcohol | 1.50 | 1.50 | 1.50 |
| Lanette ® 18 | Stearyl Alcohol | 1.00 | 1.00 | 1.00 |
| Euxyl PE9010 | Phenoxyethanol (and) Ethylhexylglycerin | 1.00 | 1.00 | 1.00 |
| Uvinul ® T150 | Ethylhexyl Triazone | 2.10 | 2.10 | 2.10 |
| BMDBM | Butyl Methoxydibenzoyl-methane | 2.50 | 2.50 | 2.50 |

TABLE 5-continued

| Trade Name | INCI-Name | Example 12 % (w/w) as supplied | Example 13 % (w/w) as supplied | Example 14 % (w/w) as supplied |
|---|---|---|---|---|
| Tinosorb ® S | Bis-Ethylhexyloxyphenol Methoxyphenyl Triazine | 1.30 | | 0.50 |
| Linear UV-Absorbing Polyether (14-1-S HLS) | Polyglceryl Ester + Tinuvin | | 2.60 | 1.60 |
| Phase B | | | | |
| Water, demin. | Aqua | Qs. 100 | Qs. 100 | Qs. 100 |
| Glycerin | Glycerol | 3.00 | 3.00 | 3.00 |
| Amphisol K | Potassium Cetyl Phosphate | 2.50 | 2.50 | 2.50 |
| Keltrol CG-RD | Xanthan Gum | 0.25 | 0.25 | 0.25 |
| Edeta ® BD | Disodium EDTA | 0.20 | 0.20 | 0.20 |
| Phase C | | | | |
| Tinosorb M | Methylene Bis-Benzo-triazolyl Tetramethylbutylphenol (nano) (and) Aqua (and) Decyl Glucoside (and) Propylene Glycol (and) Xanthan Gum | 4.00 | 4.00 | 4.00 |
| Tinosorb A2B | Tris-Biphenyl Triazine (nano) (and) Aqua (and) Decyl Glucoside (and) Butylene Glycol (and) Disodium Phosphate (and) Xanthan Gum | 5.00 | 5.00 | 5.00 |
| SPF (in silico) | | 33.4 | 33.4 | 33.4 |
| UVA-PF (in silico) | | 12.4 | 11.3 | 11.8 |

COMPOSITION EXAMPLES 15-16. Examples 15-16 illustrate the linear UV-Absorbing Polyether can be formulated with other UV absorbing compounds. The linear UV-Absorbing polyether was made consistent with the method described in Example 3B and Example 4A. Examples 15-16b were prepared using a standard sunscreen emulsion as shown in Table 6 described below by heating up phase A and phase B (first phase B without Tinovis GTC, add under stirring) to 75° C. under stirring. (to solve all crystaline ingredients). Add phase A into B under homogenizer. (Ultra Turrax at speed 9500 rpm, time 90 sec). Cool down to room temperature under continuous stirring. (stirring with helice paddle). Meanwhile, in case of order, mix phase C, at RT add phase C and adjust the pH approx at 6.5. Finally adjust the pH at 6.5-7.0.

TABLE 6

| Trade Name | INCI-Name | Example 15 % (w/w) as supplied | Example 16 % (w/w) as supplied | Example 16b % (w/w) as supplied |
|---|---|---|---|---|
| Phase A | | | | |
| Eumulgin B2 | Ceteareth-20 | 2.00 | 2.00 | 2.00 |
| Eldew SL-205 | Isopropyl Lauryl Sarcosinate | 10.00 | 10.00 | 10.00 |
| Cetiol AB | C12-15 Alkyl Benzoate | 30.00 | 30.00 | 30.00 |
| Euxyl PE9010 | Phenoxyethanol (and) Ethylhexylglycerin | 2.00 | 2.00 | 2.00 |
| Uvinul ® T150 | Ethylhexyl Triazone | 1.50 | 1.50 | 1.50 |
| Tinosorb ® S | Bis-Ethylhexyloxyphenol Methoxyphenyl Triazine | 1.70 | 1.70 | 1.70 |
| Linear UV-Absorbing Polyether (14-1-S HLS) | Polygiceryl Ester + Tinuvin | | 12.00 | 8.00 |
| Phase B | | | | |
| Water, demin. | Aqua | qs. to 100 | qs. to 100 | qs. to 100 |
| 1,3-Butandiol | Butylene Glycol | 2.00 | 2.00 | 2.00 |
| Tinovis GTC | Acrylates/Beheneth-25 Methylacrylate copolymer | 2.00 | 2.00 | 2.00 |
| EDTA ® BD | Disodium EDTA | 0.20 | 0.20 | 0.20 |
| Phase C | | | | |
| Tinosorb ® M | Tris-Biphenyl Triazine | 6.00 | | 2.00 |
| Tinsorb ® A2B | Methylene Bis-Benzo-triazolyl Tetramethyl-butylphenol | 6.00 | 6.00 | 6.00 |
| SPF (in silico) | | 33.7 | 50.5 | 46 |
| UVA-PF (in silico) | | 11.2 | 14.1 | 13.5 |

COMPOSITION EXAMPLES 17-21. Examples 17-21 illustrate the linear UV-Absorbing Polyether can be formulated with other UV absorbing compounds. The linear UV-Absorbing polyether was made consistent with the method described in Example 3B and Example 4A. Examples 17-21 were prepared using a standard sunscreen emulsion as shown in Table 7 described below by heating upheat up phase A to 75° C. under stirring followed by heating up phase B without Amphisol K to 75° C. under stirring. At 75° C. add Amphisol K into Phase B, continue stirring. Add phase A into phase B under stirring, homogenize. Cool down to RT, add the ingredients of phase C. pH value 6.1-6.5.

TABLE 7

| Trade Name | INCI-Name | Example 17 % (w/w) as supplied | Example 18 % (w/w) as supplied | Example 19 % (w/w) as supplied | Example 20 % (w/w) as supplied | Example 21 % (w/w) as supplied |
|---|---|---|---|---|---|---|
| Phase A | | | | | | |
| Cetiol ® OE | Dicaprylyl Ether | 6.00 | 6.00 | 6.00 | 6.00 | 6.00 |
| Isopropyl Palmitate | Isopropyl Palmitate | 5.00 | 5.00 | 5.00 | 5.00 | 5.00 |
| Cetiol ® AB | C12-15 Alkyl Benzoate | 4.00 | 4.00 | 4.00 | 4.00 | 4.00 |
| Antaron V-220 | VP/Eicosene Copolymer | 4.00 | 4.00 | 4.00 | 4.00 | 4.00 |
| Lanette ® 22 | Behenyl Alcohol | 2.50 | 2.50 | 2.50 | 2.50 | 2.50 |
| Uvinul ® MC 80 | Ethylhexyl Methoxycinnamate | 7.00 | 7.00 | 10.00 | 7.00 | 10.00 |

TABLE 7-continued

| Trade Name | INCI-Name | Example 17 % (w/w) as supplied | Example 18 % (w/w) as supplied | Example 19 % (w/w) as supplied | Example 20 % (w/w) as supplied | Example 21 % (w/w) as supplied |
|---|---|---|---|---|---|---|
| Uvinul ® T150 | Ethylhexyl Triazone | | | 2.00 | | 2.00 |
| Uvinul ® A Plus | Diethylamino Hydroxybenzoyl Hexyl Benzoate | 4.00 | 4.00 | 10.00 | 4.00 | 10.00 |
| Tinosorb ® S | Bis-Ethylhexyloxyphenol Methoxyphenyl Triazine | | | | | 1.00 |
| Linear UV-Absorbing Polyether (14-1-S HLS) Phase B | Polyglceryl Ester + Tinuvin | | 1.00 | 4.00 | 0.50 | 2.00 |
| Water, demin. | Aqua | Qs. 100 | Qs. 100 | Qs. 100 | Qs. 100 | Qs. 100 |
| Amphisol K | Potassium Cetyl Phosphate | 2.50 | 2.50 | 2.50 | 2.50 | 2.50 |
| Edeta ® BD | Disodium EDTA | 0.20 | 0.20 | 0.20 | 0.20 | 0.20 |
| Keltrol CG-RD Phase C | Xantham Gum | 0.15 | 0.15 | 0.15 | 0.15 | 0.15 |
| Xiameter PMX-200 Silicone Fluid 1CS | Dimethicone | 5.00 | 5.00 | 5.00 | 5.00 | 5.00 |
| Tinosorb ®S Aqua | Aqua, Bis-Ethylhexyloxyphenol Methoxyphenyl Triazine, Polymethyl Methacrylate, Sodium Laureth Sulfate, Aminomethyl Propanol | 5.00 | | | 2.50 | |
| Preservative | | qs | qs | qs | qs | qs |
| | SPF (in silico) | 23.4 | 21.4 | 47.6 | 21.8 | 45.2 |
| | UVA-PF (in silico) | 9.9 | 8.7 | 19 | 9 | 18.2 |

COMPOSITION EXAMPLES 22-23. Examples 22-23 illustrate the linear UV-Absorbing Polyether can be formulated with other UV absorbing compounds. The linear UV-Absorbing polyether was made consistent with the method described in Example 3B and Example 4A. Examples 22-23 were prepared using a standard sunscreen emulsion as shown in Table 8 described below by heating phase A to 75° C. under stirring followed by heating phase B to 75° C. under stirring. Add phase A to B under stirring, homogenize. Cool down under stirring, below 40° C. add phase C. Continue stirring. pH value 5.6-6.5

TABLE 8

| Trade Name | INCI-Name | Example 22 % (w/w) as supplied | Example 23 % (w/w) as supplied |
|---|---|---|---|
| Phase A | | | |
| Dehymuls PGPH | Polyglyceryl-2-Dipolyhydroxystearate | 4.00 | 4.00 |
| Cetiol B | Dibutyl Adipate | 10.00 | 10.00 |
| Cetion AB | C12-15 Alkyl Benzoate | 5.00 | 5.00 |
| Lanette O | Cetearyl Alcohol | 2.50 | 2.50 |
| Uvinul ® MC 80 | Ethylhexyl Methoxycinnamate | 9.50 | 9.50 |
| Uvinul ® T150 | Ethylhexyl Triazone | 2.50 | 2.50 |
| Uvinul ® A Plus | Diethylamino Hydroxybenzoyl Hexyl Benzoate | 10.00 | 10.00 |
| Tinosorb ® S | Bis-Ethylhexyloxyphenol Methoxyphenyl Triazine | 1.00 | |
| Linear UV-Absorbing Polyether (14-1-S HLS) Phase B | Polygiceryl Ester + Tinuvin | | 2.00 |
| Water, demin. | Aqua | Qs. 100 | Qs. 100 |
| Glycerin | Glycerin | 3.00 | 3.00 |
| Plantapon ® LGC SORB | Sodium Lauryl Glucose Carboxylate (and) Lauryl Glucoside | 1.50 | 1.50 |

TABLE 8-continued

| Trade Name | INCI-Name | Example 22 % (w/w) as supplied | Example 23 % (w/w) as supplied |
|---|---|---|---|
| Cosmedia ® SP | Sodium Polyacrylate | 0.80 | 0.80 |
| Edeta ® BD | Disodium EDTA | 0.20 | 0.20 |
| Keltrol CG-RD | Xantham Gum | 0.15 | 0.15 |
| Phase C | | | |
| Tinosorb ®M | Methylene Bis-Benzotriazolyl Tetramethylbutylphenol | 4.00 | |
| Preservative | | qs | qs |
| SPF (in silico) | | 50.9 | 50.6 |
| UVA-PF (in silico) | | 21.2 | 20.9 |

COMPOSITION EXAMPLES 24-25. Examples 24-25 illustrate the linear UV-Absorbing Polyether can be formulated with other UV absorbing compounds. The linear UV-Absorbing polyether was made consistent with the method described in Example 3B and Example 4A.

Examples 24-25 were prepared using a standard sunscreen emulsion as shown in Table 9 described below by heating up phases A and B to 75° C. At 75° C. add phase B into A under quick stirring. Under 40° C. add phase C. Cool down to RT, then add phase D in the given order.

TABLE 9

| Trade Name | INCI-Name | Example 24 % (w/w) as supplied | Example 25 % (w/w) as supplied |
|---|---|---|---|
| Phase A | | | |
| Dehymuls LE | PEG-30 Dipolyhydroxystearate | 4.00 | 4.00 |
| Cetiol CC | Dicaprylyl Carbonate | 12.00 | 12.00 |
| Cetiol B | Dibutyl Adipate | 6.00 | 6.00 |
| Uvinul ® MC 80 | Ethylhexyl Methoxycinnamate | 7.50 | 7.50 |
| Uvinul ® A Plus | Diethylamino Hydroxybenzoyl Hexyl Benzoate | 7.00 | 7.00 |
| Tinosorb ® S | Bis-Ethylhexyloxyphenol Methoxyphenyl Triazine | 2.50 | |
| Linear UV-Absorbing Polyether (14-1-S HLS) | Polygiceryl Ester + Tinuvin | | 5.00 |
| Phase B | | | |
| Water, demin. | Aqua | Qs. 100 | Qs. 100 |
| Butylene Glycol | Butylene Glycol | 3.00 | 3.00 |
| Sodium Chloride | Sodium Chloride | 1.00 | 1.00 |
| Edeta BD | Disodium EDTA | 0.10 | 0.10 |
| Phase C | | | |
| Tinosorb ® A2B | Tris-Biphenyl Triazine | 10.0 | 10.0 |
| Phase D | | | |
| Xiameter PMX-200 Silicone Fluid 1CS | Dimethicone | 22.00 | 22.00 |
| Ethanol | Alcohol | 8.00 | 8.00 |
| Orasol 2002 D NAT COS | Nylon-12 | 2.00 | 2.00 |
| Preservative | | qs. | qs. |
| SPF (in silico) | | 51.1 | 50.4 |
| UVA-PF (in silico) | | 18.4 | 17.7 |

TABLE 10

| INCI | Example 26 % w/w | Example 27 % w/w | Example 28 % w/w |
|---|---|---|---|
| Ceateryl Glucoside (nad) Cetearyl Alcohol | 4.00 | 4.00 | 4.00 |
| Disodium Cetearyl Sulfosuccinate | 1.00 | 1.00 | 1.00 |
| C12-15 Alkyl Benzoate | 8.00 | 8.00 | 8.00 |
| Dibutyl Adipate | 8.00 | 8.00 | 8.00 |
| Coco-Caprylate | 4.00 | 4.00 | 4.00 |
| Pentaerythrityl Distearate | 1.00 | 1.00 | 1.00 |
| Bis-Ethylhexyloxyphenol Methoxyphenyl Triazine | 2.00 | 2.00 | |
| Linear UV-Absorbing Polyether (14-1-S HLS) | | | 4.00 |
| Aqua | Qs. 100 | Qs. 100 | Qs. 100 |
| Glycerin | 3.00 | 3.00 | 3.00 |
| Di Na EDTA | 0.20 | 0.20 | 0.20 |
| Xanthan Gum | 0.40 | 0.40 | 0.40 |
| Phenoxyethanol | 1.00 | 1.00 | 1.00 |
| Carbomer | 0.15 | 0.15 | 0.15 |
| Methylene Bis-Benzotriazolyl Tetramethylbutylphenol | 4.00 | 4.00 | 4.00 |
| Aqua, Bis-Ethylhexyloxyphenol Methoxyphenyl Triazine, Polymethyl Methacrylate, Sodium Laureth Sulfate, Aminomethyl Propanol | 5.00 | 5.00 | 5.00 |
| 1,1'-(1,4-piperazinediyl)bis[1-[2-[4-(diethylamino)-2-hydroxybenzoyl]phenyl]-methanone | | 8.00 | |
| Silica | 1.00 | 1.00 | 1.00 |
| Polyamide-5 | 2.00 | 2.00 | 2.00 |
| Tetrahydroxypropyl Ethylenediamine | 0.80 | 1.00 | 0.80 |
| SPF in silico | 11.0 | 14.2 | 11.2 |
| UVA-PF (in silico) | 10.2 | 11.4 | 9.9 |

TABLE 11

| INCI | Example 29 % w/w | Example 30 % w/w | Example 31 % w/w |
|---|---|---|---|
| Ceateryl Glucoside (nad) Cetearyl Alcohol | 4.00 | 4.00 | 4.00 |
| Disodium Cetearyl Sulfosuccinate | 1.00 | 1.00 | 1.00 |
| C12-15 Alkyl Benzoate | 8.00 | 8.00 | 8.00 |
| Dibutyl Adipate | 8.00 | 8.00 | 8.00 |
| Coco-Caprylate | 4.00 | 4.00 | 4.00 |
| Pentaerythrityl Distearate | 1.00 | 1.00 | 1.00 |
| Bis-Ethylhexyloxyphenol Methoxyphenyl Triazine | | 1.00 | 1.00 |
| Linear UV-Absorbing Polyether (14-1-S HLS) | 4.00 | 2.00 | 2.00 |
| Aqua | Qs. 100 | Qs. 100 | Qs. 100 |
| Glycerin | 3.00 | 3.00 | 3.00 |
| Di Na EDTA | 0.20 | 0.20 | 0.20 |
| Xanthan Gum | 0.40 | 0.40 | 0.40 |
| Phenoxyethanol | 1.00 | 1.00 | 1.00 |
| Carbomer | 0.15 | 0.15 | 0.15 |
| Methylene Bis-Benzotriazolyl Tetramethylbutylphenol | 4.00 | 4.00 | 4.00 |
| Aqua, Bis-Ethylhexyloxyphenol Methoxyphenyl Triazine, Polymethyl Methacrylate, Sodium Laureth Sulfate, Aminomethyl Propanol | 5.00 | 5.00 | 5.00 |
| 1,1'-(1,4-piperazinediyl)bis[1-[2-[4-(diethylamino)-2-hydroxybenzoyl]phenyl]-methanone | 8.00 | | 8.00 |
| Silica | 1.00 | 1.00 | 1.00 |
| Polyamide-5 | 2.00 | 2.00 | 2.00 |
| Tetrahydroxypropyl Ethylenediamine | 1.00 | 0.80 | 1.00 |
| SPF in silico | 13.8 | 11.2 | 14.1 |
| UVA-PF (in silico) | 18.5 | 10.2 | 19.0 |

TABLE 12

| INCI | Example 32 % w/w | Example 33 % w/w | Example 34 % w/w |
|---|---|---|---|
| Ceateryl Glucoside (and) Cetearyl Alcohol | 4.00 | 4.00 | 4.00 |
| Disodium Cetearyl Sulfosuccinate | 1.50 | 1.50 | 1.50 |
| C12-15 Alkyl Benzoate | 8.00 | 8.00 | 8.00 |
| Dibutyl Adipate | 8.00 | 8.00 | 8.00 |
| Diisopropyl Sebacate | 5.00 | 5.00 | 5.00 |
| Coco-Caprylate | 4.00 | 4.00 | 4.00 |
| Pentaerythrityl Distearate | 1.00 | 1.00 | 1.00 |
| Diethylamino Hydroxybenzoyl Hexyl Benzoate | 3.00 | 3.00 | 8.00 |
| Ethylhexyl Triazone | 2.00 | 2.00 | 2.00 |
| Bis-Ethylhexyloxyphenol Methoxyphenyl Triazine | 2.00 | 2.00 | |
| Linear UV-Absorbing Polyether (14-1-S HLS) | | | 4.00 |
| Aqua | Qs. 100 | Qs. 100 | Qs. 100 |
| Glycerin | 3.00 | 3.00 | 3.00 |
| Di Na EDTA | 0.20 | 0.20 | 0.20 |
| Xanthan Gum | 0.40 | 0.40 | 0.40 |
| Phenoxyethanol | 1.00 | 1.00 | 1.00 |
| Carbomer | 0.15 | 0.15 | 0.15 |
| Aqua, Bis-Ethylhexyloxyphenol Methoxyphenyl Triazine, Polymethyl Methacrylate, Sodium Laureth Sulfate, Aminomethyl Propanol | 7.50 | 7.50 | 7.50 |
| 1,1'-(1,4-piperazinediyl)bis[1-[2-[4-(diethylamino)-2-hydroxybenzoyl]phenyl]-methanone | | 20.00 | |
| Silica | 1.00 | 1.00 | 1.00 |
| Polyamide-5 | 2.00 | 2.00 | 2.00 |
| Tetrahydroxypropyl Ethylenediamine | 0.80 | 0.80 | 0.80 |
| SPF in silico | 22.7 | 32.9 | 23.1 |
| UVA-PF (in silico) | 13.7 | 35.6 | 13.5 |

TABLE 13

| INCI | Example 35 % w/w | Example 36 % w/w | Example 37 % w/w |
|---|---|---|---|
| Ceateryl Glucoside (and) Cetearyl Alcohol | 4.00 | 4.00 | 4.00 |
| Disodium Cetearyl Sulfosuccinate | 1.50 | 1.50 | 1.50 |
| C12-15 Alkyl Benzoate | 8.00 | 8.00 | 8.00 |
| Dibutyl Adipate | 8.00 | 8.00 | 8.00 |
| Diisopropyl Sebacate | 5.00 | 5.00 | 5.00 |
| Coco-Caprylate | 4.00 | 4.00 | 4.00 |
| Pentaerythrityl Distearate | 1.00 | 1.00 | 1.00 |
| Diethylamino Hydroxybenzoyl Hexyl Benzoate | 3.00 | 8.00 | 3.00 |
| Ethylhexyl Triazone | 2.00 | 2.00 | 2.00 |
| Bis-Ethylhexyloxyphenol Methoxyphenyl Triazine | | 1.00 | 1.00 |
| Linear UV-Absorbing Polyether (14-1-S HLS) | 4.00 | 2.00 | 2.00 |
| Aqua | Qs. 100 | Qs. 100 | Qs. 100 |
| Glycerin | 3.00 | 3.00 | 3.00 |
| Di Na EDTA | 0.20 | 0.20 | 0.20 |
| Xanthan Gum | 0.40 | 0.40 | 0.40 |
| Phenoxyethanol | 1.00 | 1.00 | 1.00 |
| Carbomer | 0.15 | 0.15 | 0.15 |
| Aqua, Bis-Ethylhexyloxyphenol Methoxyphenyl Triazine, Polymethyl Methacrylate, Sodium Laureth Sulfate, Aminomethyl Propanol | 7.50 | 7.50 | 7.50 |
| 1,1'-(1,4-piperazinediyl)bis[1-[2-[4-(diethylamino)-2-hydroxybenzoyl]phenyl]-methanone | 20.00 | | 20.00 |
| Silica | 1.00 | 1.00 | 1.00 |
| Polyamide-5 | 2.00 | 2.00 | 2.00 |
| Tetrahydroxypropyl Ethylenediamine | 0.80 | 0.80 | 0.80 |
| SPF in silico | 32.6 | 23.0 | 32.7 |
| UVA-PF (in silico) | 34.6 | 13.7 | 35.1 |

TABLE 14

| INCI | Example 38 % w/w | Example 39 % w/w | Example 40 % w/w |
|---|---|---|---|
| Ceteareth-20 | 1.50 | 1.50 | 1.50 |
| Disodium Cetearyl Sulfosuccinate | 2.50 | 2.50 | 2.50 |
| Dibutyl Adipate | 11.00 | 11.00 | 11.00 |
| Diisopropyl Sebacate | 7.00 | 7.00 | 7.00 |
| Diethylamino Hydroxybenzoyl Hexyl Benzoate | 8.00 | 8.00 | 8.00 |
| Ethylhexyl Triazone | 3.00 | 3.00 | 3.00 |
| Bis-Ethylhexyloxyphenol Methoxyphenyl Triazine | 2.00 | 2.00 | |
| Linear UV-Absorbing Polyether (14-1-S HLS) | | | 4.00 |
| Aqua | Qs. 100 | Qs. 100 | Qs. 100 |
| Di Na EDTA | 0.20 | 0.20 | 0.20 |
| Xanthan Gum | 0.50 | 0.50 | 0.50 |
| Phenoxyethanol | 1.00 | 1.00 | 1.00 |
| Phenylbenzimidazole Sulfonic Acid Aqua | 1.00 | 1.00 | 1.00 |
| Tetrahydroxypropyl Ethylenediamine | 2.90 | 2.90 | 2.90 |
| Methylene Bis-Benzotriazolyl Tetramethylbutylphenol | 6.00 | 6.00 | 6.00 |
| Aqua, Bis-Ethylhexyloxyphenol Methoxyphenyl Triazine, Polymethyl Methacrylate, Sodium Laureth Sulfate, Aminomethyl Propanol | 10.00 | 10.00 | 10.00 |
| 1,1'-(1,4-piperazinediyl)bis[1-[2-[4-(diethylamino)-2-hydroxybenzoyl]phenyl]-methanone | | 20.00 | |
| Polymethyl Methacrylate | 2.00 | 2.00 | 2.00 |
| SPF in silico | 51.7 | 61.2 | 51.8 |
| UVA-PF (in silico) | 37.7 | 64.0 | 37.5 |

TABLE 15

| INCI | Example 41 % w/w | Example 42 % w/w | Example 43 % w/w |
|---|---|---|---|
| Ceteareth-20 | 1.50 | 1.50 | 1.50 |
| Disodium Cetearyl Sulfosuccinate | 2.50 | 2.50 | 2.50 |
| Dibutyl Adipate | 11.00 | 11.00 | 11.00 |
| Diisopropyl Sebacate | 7.00 | 7.00 | 7.00 |
| Diethylamino Hydroxybenzoyl Hexyl Benzoate | 8.00 | 8.00 | 8.00 |
| Ethylhexyl Triazone | 3.00 | 3.00 | 3.00 |
| Bis-Ethylhexyloxyphenol Methoxyphenyl Triazine | | 1.00 | 1.00 |
| Linear UV-Absorbing Polyether (14-1-S HLS) | 4.00 | 2.00 | 2.00 |
| Aqua | Qs. 100 | Qs. 100 | Qs. 100 |
| Di Na EDTA | 0.20 | 0.20 | 0.20 |
| Xanthan Gum | 0.50 | 0.50 | 0.50 |
| Phenoxyethanol | 1.00 | 1.00 | 1.00 |
| Phenylbenzimidazole Sulfonic Acid Aqua | 1.00 | 1.00 | 1.00 |
| Tetrahydroxypropyl Ethylenediamine | 2.90 | 2.90 | 2.90 |
| Methylene Bis-Benzotriazolyl Tetramethylbutylphenol | 6.00 | 6.00 | 6.00 |
| Aqua, Bis-Ethylhexyloxyphenol Methoxyphenyl Triazine, Polymethyl Methacrylate, Sodium Laureth Sulfate, Aminomethyl Propanol | 10.00 | 10.00 | 10.00 |
| 1,1'-(1,4-piperazinediyl)bis[1-[2-[4-(diethylamino)-2-hydroxybenzoyl]phenyl]-methanone | 20.00 | | 20.00 |
| Polymethyl Methacrylate | 2.00 | 2.00 | 2.00 |
| SPF in silico | 60.9 | 51.7 | 61.1 |
| UVA-PF (in silico) | 63.1 | 37.7 | 63.5 |

It is understood that while the invention has been described in conjunction with the detailed description thereof, that the foregoing description is intended to illustrate and not limit the scope of the invention.

The invention claimed is:

1. A sunscreen composition, comprising:
    a polymer composition comprising a linear, ultraviolet radiation absorbing polyether comprising a covalently bound UV-chromophore that is a benzotriazole; and
    a mixture of Bis Ethylhexyloxyphenol Methoxyphenyl Triazine, Ethylhexyl Triazone, Methylene Bis-Benzotriazolyl Tetramethylbutylphenol, Diethylamino Hydroxybenzoyl Hexyl Benzoate, and titanium dioxide, wherein the composition comprises about 5 to about 15 weight percent of the ultraviolet radiation absorbing polyether; about 0.5 weight percent of Bis Ethylhexyloxyphenol Methoxyphenyl Triazine, about 2.5 weight percent of Ethylhexyl Triazone, about 4 weight percent of Methylene Bis-Benzotriazolyl Tetramethylbutylphenol, about 2 weight percent of Diethylamino Hydroxybenzoyl Hexyl Benzoate, and about 0.5 weight percent titanium dioxide.

* * * * *